(12) United States Patent
Bazin-Lee et al.

(10) Patent No.: US 8,575,340 B2
(45) Date of Patent: Nov. 5, 2013

(54) PURINE DERIVATIVES AND THEIR PHARMACEUTICAL USES

(75) Inventors: Helene Bazin-Lee, Hamilton, MT (US); Diane Mary Coe, Stevenage (GB); David A. Johnson, Hamilton, MT (US); Charlotte Jane Mitchell, Stevenage (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/578,008

(22) PCT Filed: Feb. 8, 2011

(86) PCT No.: PCT/EP2011/051828
§ 371 (c)(1),
(2), (4) Date: Aug. 9, 2012

(87) PCT Pub. No.: WO2011/098451
PCT Pub. Date: Aug. 18, 2011

(65) Prior Publication Data
US 2012/0315291 A1    Dec. 13, 2012

Related U.S. Application Data

(60) Provisional application No. 61/303,005, filed on Feb. 10, 2010.

(51) Int. Cl.
| A61K 31/52 | (2006.01) |
| C07D 473/18 | (2006.01) |
| A61P 31/00 | (2006.01) |
| A61P 35/00 | (2006.01) |
| A61P 37/08 | (2006.01) |
| A61P 29/00 | (2006.01) |
| A61P 37/04 | (2006.01) |
| A61P 11/06 | (2006.01) |

(52) U.S. Cl.
USPC ............... 544/276; 514/263.22; 514/252.16; 424/184.1

(58) Field of Classification Search
USPC ......... 544/276; 424/184.1; 514/263.2, 252.16
See application file for complete search history.

(56) References Cited

U.S. PATENT DOCUMENTS

| 2001/0020030 A1 | 9/2001 | Stewart et al. |
| 2003/0236216 A1 | 12/2003 | Devos et al. |

FOREIGN PATENT DOCUMENTS

| EP | 0 773 023 | 5/1997 |
| EP | 1 043 021 | 10/2000 |
| EP | 1 939 198 | 7/2008 |
| EP | 2 138 497 | 12/2009 |
| WO | 95/33750 | 12/1995 |
| WO | 00/43394 | 7/2000 |
| WO | 01/49688 | 7/2001 |
| WO | 2005/002520 | 1/2005 |
| WO | 2005/020892 | 3/2005 |
| WO | 2005/025583 | 3/2005 |
| WO | 2006/117670 | 11/2006 |
| WO | 2007/028129 | 3/2007 |
| WO | 2007/041863 | 4/2007 |
| WO | 2007/093901 | 8/2007 |
| WO | 2007/142755 | 12/2007 |
| WO | 2008/101867 | 8/2008 |
| WO | 2008/114008 | 9/2008 |
| WO | 2010/018130 | 2/2010 |
| WO | 2010/018131 | 2/2010 |
| WO | 2010/018132 | 2/2010 |
| WO | 2010/018133 | 2/2010 |
| WO | 2010/018134 | 2/2010 |
| WO | 2011/017611 | 2/2011 |

OTHER PUBLICATIONS

Tao, B., Treatment of allergic airway inflammation and hyper-responsiveness by imiquimod modulating transcription factors T-bet and GATA-3, Chin. Med. J. 2006; 119(8): 640-648.*
Akira, S., Toll-like receptors: critical proteins linking innate and acquired immunity, Nat. Immuno. 2001; 2(8); 675-680.*
Liu, Y-J., IPC: Professional Type 1 Interferon-Producing Cells and Plasmacytoid Dendridic Cell Precursors, Ann. Rev. Immunol., 2005; 23: 275-306.*
Ma, R., Additive effects of CpG ODN and R-848 as adjuvants on augmenting immune responses to HBsAg vaccination, Biochem. Biophys, Res. Commun., 2007; 361: 537-542.*
Hirota et al.; Discovery of 8-Hydroxyadenines as a Novel Type of Interferon Inducer; J. Med. Chem.; 2002; vol. 45, No. 25; pp. 5419-5422; American Chemical Society.

(Continued)

*Primary Examiner* — Kortney L Klinkel
*Assistant Examiner* — John Mauro
(74) *Attorney, Agent, or Firm* — Kathryn L. Coulter

(57) ABSTRACT

The present invention relates to compounds of formula (I):

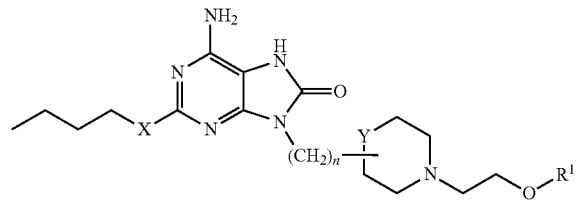

wherein;
R¹ represents hydrogen or $C_{1-3}$alkyl;
n is an integer having a value of 1 to 5;
X represents O or NH;
Y represents C or N;
or a pharmaceutically acceptable salt thereof, have been shown to be inducers of human interferon and may possess an improved profile with respect to known inducers of human interferon, for example enhanced potency. The compounds of the invention may therefore be useful in the treatment of various disorders, in particular the treatment of infectious diseases, cancer, allergic diseases and other inflammatory conditions, and their use as vaccine adjuvants.

7 Claims, No Drawings

(56) References Cited

OTHER PUBLICATIONS

Isobe et al.; Synthesis and Biological Evaluation of Novel 9-Substituted-8-hydroxadenine Derivatives asPotent Interferon Inducers; J. Med. Chem.; 2006; vol. 49, No. 6; pp. 2088-2095; American Chemical Society.

Kurimoto et al.; Prodrugs of 9-Benzyl-8-hydroxy-2-(2-hydroxyethylthio)adenine: Potent Interferon Inducing Agents in Monkeys; Chem. Pharm. Bull.; 2004; vol. 52, No. 4; pp. 466-469; Pharmaceutical Society of Japan.

* cited by examiner

PURINE DERIVATIVES AND THEIR PHARMACEUTICAL USES

CROSS-REFERENCE TO RELATED APPLICATIONS

This application is filed pursuant to 35 U.S.C. §371 as a United States National Phase Application of International Patent Application No. PCT/EP2011/051828 filed Feb. 8, 2011, which claims priority from Provisional Application No. 61/303,005 filed Feb. 10, 2010.

BACKGROUND OF THE INVENTION

The present invention relates to compounds, processes for their preparation, compositions containing them, to their use in the treatment of various disorders in particular allergic diseases and other inflammatory conditions for example allergic rhinitis and asthma, infectious diseases, cancer, and as vaccine adjuvants.

Vertebrates are constantly threatened by the invasion of microorganisms and have evolved mechanisms of immune defence to eliminate infective pathogens. In mammals, this immune system comprises two branches; innate immunity and acquired immunity. The first line of host defence is the innate immune system, which is mediated by macrophages and dendritic cells. Acquired immunity involves the elimination of pathogens at the late stages of infection and also enables the generation of immunological memory. Acquired immunity is highly specific, due to the vast repertoire of lymphocytes with antigen-specific receptors that have undergone gene rearrangement.

The innate immune response was originally thought to be non-specific, but is now known to be able to discriminate between self and a variety of pathogens. The innate immune system recognises microbes via a limited number of germline-encoded Pattern-Recognition Receptors (PRRs) which have a number of important characteristics.

Toll-like receptors (TLRs) are a family of ten Pattern Recognition Receptors described in man. TLRs are expressed predominantly by innate immune cells where their role is to monitor the environment for signs of infection and, on activation, mobilise defence mechanisms aimed at the elimination of invading pathogens. The early innate immune-responses triggered by TLRs limit the spread of infection, while the pro-inflammatory cytokines and chemokines that they induce lead to recruitment and activation of antigen presenting cells, B cells, and T cells. The TLRs can modulate the nature of the adaptive immune-responses to give appropriate protection via dendritic cell-activation and cytokine release (Akira S. et al, *Nat. Immunol.*, 2001: 2, 675-680). The profile of the response seen from different TLR agonists depends on the cell type activated.

TLR7 is a member of the subgroup of TLRs (TLRs 3, 7, 8, and 9), localised in the endosomal compartment of cells which have become specialised to detect non-self nucleic acids. TLR7 plays a key role in anti-viral defence via the recognition of ssRNA (Diebold S. S. et al, Science, 2004: 303, 1529-1531; and Lund J. M. et al, PNAS, 2004: 101, 5598-5603). TLR7 has a restricted expression-profile in man and is expressed predominantly by B cells and plasmacytoid dendritic cells (pDC), and to a lesser extent by monocytes. Plasmacytoid DCs are a unique population of lymphoid-derived dendritic cells (0.2-0.8% of Peripheral Blood Mononuclear Cells (PBMCs)) which are the primary type I interferon-producing cells secreting high levels of interferon-alpha (IFNα) and interferon-beta (IFNβ) in response to viral infections (Liu Y-J, *Annu. Rev. Immunol.*, 2005: 23, 275-306).

Allergic diseases are associated with a Th2-biased immune-response to allergens. Th2 responses are associated with raised levels of IgE, which, via its effects on mast cells, promotes a hypersensitivity to allergens, resulting in the symptoms seen, for example, in allergic rhinitis. In healthy individuals the immune-response to allergens is more balanced with a mixed Th2/Th1 and regulatory T cell response. TLR7 ligands have been shown to reduce Th2 cytokine and enhance Th1 cytokine release in vitro and to ameliorate Th2-type inflammatory responses in allergic lung models in vivo (Fili L. et al, *J. All. Clin. Immunol.*, 2006: 118, 511-517; Moisan J. et al, *Am. J. Physiol. Lung Cell Mol. Physiol.*, 2006: 290, L987-995; Tao et al, *Chin. Med. J.*, 2006: 119, 640-648). Thus TLR7 ligands have the potential to rebalance the immune-response seen in allergic individuals and lead to disease modification.

Central to the generation of an effective innate immune response in mammals are mechanisms which bring about the induction of interferons and other cytokines which act upon cells to induce a number of effects. These effects can include the activation of anti-infective gene expression, the activation of antigen presentation in cells to drive strong antigen-specific immunity and the promotion of phagocytosis in phagocytic cells.

Interferon was first described as a substance which could protect cells from viral infection (Isaacs & Lindemann, *J. Virus Interference. Proc. R. Soc. Lon. Ser. B. Biol. Sci.*, 1957: 147, 258-267). In man, the type I interferons are a family of related proteins encoded by genes on chromosome 9 and encoding at least 13 isoforms of interferon alpha (IFNα) and one isoform of interferon beta (IFNβ). Recombinant IFNα was the first approved biological therapeutic and has become an important therapy in viral infections and in cancer. As well as direct antiviral activity on cells, interferons are known to be potent modulators of the immune response, acting on cells of the immune system.

As a first-line therapy for hepatitis C virus (HCV) disease, interferon combinations can be highly effective at reducing viral load and in some subjects in eliminating viral replication. However, many patients fail to show a sustained viral response and in these patients viral load is not controlled. Additionally, therapy with injected interferon may be associated with a number of unwanted adverse effects which are shown to affect compliance (Dudley T, et al, *Gut.*, 2006: 55(9), 1362-3).

Administration of a small molecule compound which could stimulate the innate immune response, including the activation of type I interferons and other cytokines, could become an important strategy for the treatment or prevention of human diseases including viral infections. This type of immunomodulatory strategy has the potential to identify compounds which may be useful not only in infectious diseases but also in cancer (Krieg., *Curr. Oncol. Rep.*, 2004: 6(2), 88-95), allergic diseases (Moisan J. et al, *Am. J. Physiol. Lung Cell Mol. Physiol.*, 2006: 290, L987-995), other inflammatory conditions such as irritable bowel disease (Rakoff-Nahoum S., *Cell.*, 2004, 23, 118(2): 229-41), and as vaccine adjuvants (Persing et al., *Trends Microbiol.*, 2002: 10 (10 Suppl), S32-7).

In animal models, imiquimod demonstrated adjuvant activities either topically (Adams S. et al, *J. Immunol.*, 2008, 181:776-84; Johnston D. et al, *Vaccine*, 2006, 24:1958-65), or systemically (Fransen F. et al, *Infect. Immun.*, 2007, 75:5939-46). Resiquimod and other related TLR7/8 agonists have also been shown to display adjuvant activity (Ma R. et al, *Bio-* chem. Biophys. Res. Commun., 2007, 361:537-42; Wille-Reece U. et al, Proc. Natl. Acad. Sci. USA, 2005, 102:15190-4; Wille-Reece U. et al, US2006045885 A1).

Mechanisms which lead to induction of type I interferons are only partly understood. One mechanism which can lead to the induction of interferon in many cell types is the recognition of double-stranded viral RNA by the RNA helicases RIG-I and MDA5. This mechanism is thought to be the primary mechanism by which interferons are induced by Sendai virus infection of cells.

Further mechanisms for the induction of interferons are via TLR-dependent signalling events. In man, plasmacytoid dendritic cells (pDCs) are professional interferon-producing cells, able to make large amounts of interferons in response to, for example, viral infection. These pDCs are shown to preferentially express TLR7 and TLR9 and stimulation of these receptors with viral RNA or DNA respectively can induce expression of interferon alpha.

Oligonucleotide agonists of TLR7 and TLR9, and small molecule purine-based agonists of TLR7 have been described which can induce interferon alpha from these cell types in animals and in man (Takeda K. et al, Annu. Rev. Immunol., 2003: 21, 335-76). TLR7 agonists include imidazoquinoline compounds such as imiquimod and resiquimod, oxoadenine analogues and also nucleoside analogues such as loxoribine and 7-thia-8-oxoguanosine which have long been known to induce interferon alpha. International Patent Application publication number WO 2008/114008 (AstraZeneca AB/Dainippon Sumitomo Pharma Co. Ltd.) discloses 9-substituted-8-oxoadenine compounds as TLR7 modulators. U.S. provisional application No. 61/232,132 discloses 6-amino-2-butoxy-9-(N-(2-hydroxyethyl)-4-piperidinylmethyl)-8-hydroxypurine as an intermediate in the synthesis of Example 1.

It remains unclear how small molecule purine-like compounds can induce type I interferons and other cytokines since the molecular targets of these known inducers have not been identified. However, an assay strategy has been developed to characterise small molecule inducers of human interferon IFNα(regardless of mechanism) which is based on stimulation of primary human donor cells with compounds, and is disclosed herein.

BRIEF DESCRIPTION OF THE INVENTION

Certain compounds of the invention have been shown to be inducers of human interferon and may possess an improved profile with respect to known inducers of human interferon, for example enhanced potency, and may show enhanced selectivity for IFNα with respect to TNFα. For example, certain compounds of the invention indicate greater than 1000-fold selectivity for IFNαinduction over TNFα induction. Compounds which induce human interferon may be useful in the treatment of various disorders, for example the treatment of allergic diseases and other inflammatory conditions for example allergic rhinitis and asthma, the treatment of infectious diseases and cancer, and may also be useful as vaccine adjuvants.

Certain compounds of the invention are potent immunomodulators and accordingly, care should be exercised in their handling.

SUMMARY OF THE INVENTION

In a first aspect, there is provided the use of a compound of formula (I):

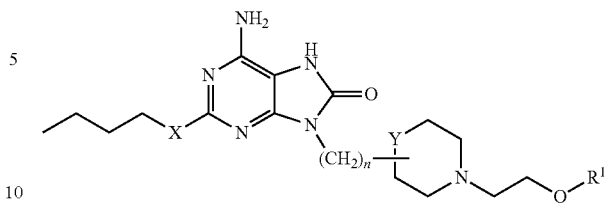

wherein;
$R^1$ represents hydrogen or $C_{1-3}$alkyl;
n is an integer having a value of 1 to 5;
X represents O or NH;
Y represents C or N;
or a pharmaceutically acceptable salt thereof as an active therapeutic agent.

In another embodiment, there is provided the use of a compound of formula (I) or a pharmaceutically acceptable salt thereof for the treatment of infectious diseases, cancer, allergic diseases and other inflammatory conditions.

In another embodiment, there is provided a compound of formula (I) or a pharmaceutically acceptable salt thereof for use as a vaccine adjuvant.

In another embodiment, there is provided the use of a compound of formula (I) or a pharmaceutically acceptable salt thereof, in the manufacture of a medicament for the treatment of infectious diseases, cancer, allergic diseases and other inflammatory conditions.

In another embodiment, there is provided a method for the treatment of infectious diseases, cancer, allergic diseases and other inflammatory conditions, which method comprises administering an effective amount of a compound of formula (I), or a pharmaceutically acceptable salt thereof.

In another embodiment, there is provided a pharmaceutical composition comprising a compound of formula (I), or a pharmaceutically acceptable salt thereof, and optionally one or more pharmaceutically acceptable diluents or carriers.

In another embodiment, there is provided a compound of formula (I) or a salt thereof, with the proviso that the compound is not 6-amino-2-butoxy-9-(N-(2-hydroxyethyl)-4-piperidinylmethyl)-8-hydroxypurine.

In a further embodiment, there is provided a compound of formula (I), or a salt thereof (or a use, a method of treatment or a composition as hereinbefore described comprising a compound of formula (I), or a pharmaceutically acceptable salt thereof), wherein $R^1$ is $C_{1-3}$alkyl.

In a further embodiment, there is provided a use, a method of treatment or a composition as hereinbefore described comprising a compound of formula (I), or a pharmaceutically acceptable salt thereof, wherein $R^1$ is hydrogen.

In a further embodiment, there is provided a compound of formula (I), or a salt thereof, wherein $R^1$ is hydrogen, with the proviso that the compound is not 6-amino-2-butoxy-9-(N-(2-hydroxyethyl)-4-piperidinylmethyl)-8-hydroxypurine.

In a further embodiment, there is provided a use, a method of treatment or a composition as hereinbefore described comprising a compound of formula (I), or a pharmaceutically acceptable salt thereof, wherein n is 1 to 4.

In a further embodiment, there is provided a compound of formula (I), or a salt thereof, wherein n is 1 to 4, with the proviso that the compound is not 6-amino-2-butoxy-9-(N-(2-hydroxyethyl)-4-piperidinylmethyl)-8-hydroxypurine.

In a further embodiment, there is provided a use, a method of treatment or a composition as hereinbefore described comprising a compound of formula (I), or a pharmaceutically acceptable salt thereof, wherein X represents O.

In a further embodiment, there is provided a compound of formula (I), or a salt thereof, wherein X represents O, with the proviso that the compound is not 6-amino-2-butoxy-9-(N-(2-hydroxyethyl)-4-piperidinylmethyl)-8-hydroxypurine.

In a further embodiment, there is provided a compound of formula (I), or a salt thereof (or a use, a method of treatment or a composition as hereinbefore described comprising a compound of formula (I), or a pharmaceutically acceptable salt thereof), wherein X represents NH.

In a further embodiment, there is provided a use, a method of treatment or a composition as hereinbefore described comprising a compound of formula (I), or a pharmaceutically acceptable salt thereof, wherein Y represents C.

In a further embodiment, there is provided a compound of formula (I), or a salt thereof, wherein Y represents C, with the proviso that the compound is not 6-amino-2-butoxy-9-(N-(2-hydroxyethyl)-4-piperidinylmethyl)-8-hydroxypurine.

In a further embodiment, there is provided a compound of formula (I), or a salt thereof (or a use, a method of treatment or a composition as hereinbefore described comprising a compound of formula (I), or a pharmaceutically acceptable salt thereof), wherein Y represents N.

In a further embodiment, there is provided a compound of formula (I), or a salt thereof (or a use, a method of treatment or a composition as hereinbefore described comprising a compound of formula (I), or a pharmaceutically acceptable salt thereof), wherein Y represents N and the $(CH_2)_n$ is connected to the six-membered ring through the nitrogen atom which is Y.

In a further embodiment, there is provided a compound of formula (I), or a salt thereof, wherein Y represents C and the $(CH_2)_n$ is connected to the six-membered ring through a carbon atom with the proviso that the compound is not 6-amino-2-butoxy-9-(N-(2-hydroxyethyl)-4-piperidinylmethyl)-8-hydroxypurine.

In a further embodiment, there is provided a compound of formula (I), or a salt thereof (or a use, a method of treatment or a composition as hereinbefore described comprising a compound of formula (I), or a pharmaceutically acceptable salt thereof), wherein Y is a carbon atom, the $(CH_2)_n$ is connected to the six-membered ring through a carbon atom and wherein the nitrogen of the 6 membered ring is ortho to the $(CH_2)_n$ group.

In a further embodiment, there is provided a compound of formula (I), or a salt thereof (or a use, a method of treatment or a composition as hereinbefore described comprising a compound of formula (I), or a pharmaceutically acceptable salt thereof), wherein Y is a carbon atom, the $(CH_2)_n$ is connected to the six-membered ring through a carbon atom and wherein the nitrogen of the 6 membered ring is meta to the $(CH_2)_n$ group.

In a further embodiment, there is provided a use, a method of treatment or a composition as hereinbefore described comprising a compound of formula (I), or a pharmaceutically acceptable salt thereof, wherein Y is a carbon atom, the $(CH_2)_n$ is connected to the six-membered ring through a carbon atom and wherein the nitrogen of the 6 membered ring is para to the $(CH_2)_n$ group.

In a further embodiment, there is provided a compound of formula (I), or a salt thereof, wherein Y is a carbon atom, the $(CH_2)_n$ is connected to the six-membered ring through a carbon atom and wherein the nitrogen of the 6 membered ring is para to the $(CH_2)_n$ group, with the proviso that the compound is not 6-amino-2-butoxy-9-(N-(2-hydroxyethyl)-4-piperidinylmethyl)-8-hydroxypurine.

In a further embodiment there is provided a compound, or a salt thereof, selected from the list consisting of:
6-Amino-2-(butyloxy)-9-{3-[1-(2-hydroxyethyl)-2-piperidinyl]propyl}-7,9-dihydro-8H-purin-8-one;
6-Amino-2-(butyloxy)-9-{[1-(2-hydroxyethyl)-3-piperidinyl]methyl}-7,9-dihydro-8H-purin-8-one;
6-Amino-2-(butyloxy)-9-{2-[1-(2-hydroxyethyl)-3-piperidinyl]ethyl}-7,9-dihydro-8H-purin-8-one;
6-Amino-2-(butyloxy)-9-{3-[1-(2-hydroxyethyl)-3-piperidinyl]propyl}-7,9-dihydro-8H-purin-8-one;
6-Amino-2-(butyloxy)-9-{4-[1-(2-hydroxyethyl)-3-piperidinyl]butyl}-7,9-dihydro-8H-purin-8-one;
6-Amino-2-(butyloxy)-9-{2-[1-(2-hydroxyethyl)-4-piperidinyl]ethyl}-7,9-dihydro-8H-purin-8-one;
6-Amino-2-(butyloxy)-9-{3-[1-(2-hydroxyethyl)-4-piperidinyl]propyl}-7,9-dihydro-8H-purin-8-one;
6-Amino-2-(butyloxy)-9-{4-[1-(2-hydroxyethyl)-4-piperidinyl]butyl}-7,9-dihydro-8H-purin-8-one;
6-Amino-2-(butyloxy)-9-{5-[1-(2-hydroxyethyl)-4-piperidinyl]pentyl}-7,9-dihydro-8H-purin-8-one;
6-Amino-2-(butyloxy)-9-{3-[4-(2-hydroxyethyl)-1-piperazinyl]propyl}-7,9-dihydro-8H-purin-8-one;
6-Amino-2-(butylamino)-9-{3-[4-(2-hydroxyethyl)-1-piperazinyl]propyl}-7,9-dihydro-8H-purin-8-one;
6-Amino-2-(butyloxy)-9-{4-[4-(2-hydroxyethyl)-1-piperazinyl]butyl}-7,9-dihydro-8H-purin-8-one;
6-Amino-2-(butylamino)-9-{4-[4-(2-hydroxyethyl)-1-piperazinyl]butyl}-7,9-dihydro-8H-purin-8-one;
6-Amino-2-(butyloxy)-9-{5-[4-(2-hydroxyethyl)-1-piperazinyl]pentyl}-7,9-dihydro-8H-purin-8-one;
6-Amino-2-(butyloxy)-9-(5-{4-[2-(methyloxy)ethyl]-1-piperazinyl}pentyl)-7,9-dihydro-8H-purin-8-one; and
6-Amino-2-(butyloxy)-9-(5-{4-[2-(ethyloxy)ethyl]-1-piperazinyl}pentyl)-7,9-dihydro-8H-purin-8-one.

In a further embodiment, there is provided a use, a method of treatment or a composition as hereinbefore described comprising a compound, or a pharmaceutically acceptable salt thereof, selected from the list consisting of:
6-Amino-2-(butyloxy)-9-{3-[1-(2-hydroxyethyl)-2-piperidinyl]propyl}-7,9-dihydro-8H-purin-8-one;
6-Amino-2-(butyloxy)-9-{[1-(2-hydroxyethyl)-3-piperidinyl]methyl}-7,9-dihydro-8H-purin-8-one;
6-Amino-2-(butyloxy)-9-{2-[1-(2-hydroxyethyl)-3-piperidinyl]ethyl}-7,9-dihydro-8H-purin-8-one;
6-Amino-2-(butyloxy)-9-{3-[1-(2-hydroxyethyl)-3-piperidinyl]propyl}-7,9-dihydro-8H-purin-8-one;
6-Amino-2-(butyloxy)-9-{4-[1-(2-hydroxyethyl)-3-piperidinyl]butyl}-7,9-dihydro-8H-purin-8-one;
6-Amino-2-(butyloxy)-9-{[1-(2-hydroxyethyl)-4-piperidinyl]methyl}-7,9-dihydro-8H-purin-8-one;
6-Amino-2-(butyloxy)-9-{2-[1-(2-hydroxyethyl)-4-piperidinyl]ethyl}-7,9-dihydro-8H-purin-8-one;
6-Amino-2-(butyloxy)-9-{3-[1-(2-hydroxyethyl)-4-piperidinyl]propyl}-7,9-dihydro-8H-purin-8-one;
6-Amino-2-(butyloxy)-9-{4-[1-(2-hydroxyethyl)-4-piperidinyl]butyl}-7,9-dihydro-8H-purin-8-one;
6-Amino-2-(butyloxy)-9-{5-[1-(2-hydroxyethyl)-4-piperidinyl]pentyl}-7,9-dihydro-8H-purin-8-one;
6-Amino-2-(butyloxy)-9-{3-[4-(2-hydroxyethyl)-1-piperazinyl]propyl}-7,9-dihydro-8H-purin-8-one;
6-Amino-2-(butylamino)-9-{3-[4-(2-hydroxyethyl)-1-piperazinyl]propyl}-7,9-dihydro-8H-purin-8-one;
6-Amino-2-(butyloxy)-9-{4-[4-(2-hydroxyethyl)-1-piperazinyl]butyl}-7,9-dihydro-8H-purin-8-one;
6-Amino-2-(butylamino)-9-{4-[4-(2-hydroxyethyl)-1-piperazinyl]butyl}-7,9-dihydro-8H-purin-8-one;

6-Amino-2-(butyloxy)-9-{5-[4-(2-hydroxyethyl)-1-piperazinyl]pentyl}-7,9-dihydro-8H-purin-8-one;
6-Amino-2-(butyloxy)-9-(5-{4-[2-(methyloxy)ethyl]-1-piperazinyl}pentyl)-7,9-dihydro-8H-purin-8-one; and
6-Amino-2-(butyloxy)-9-(5-{4-[2-(ethyloxy)ethyl]-1-piperazinyl}pentyl)-7,9-dihydro-8H-purin-8-one.

It is to be understood that the invention includes all possible combinations of embodiments and substituents described herein.

DETAILED DESCRIPTION OF THE INVENTION

References to 'alkyl' include references to both straight-chain and branched-chain aliphatic isomers of the corresponding alkyl, suitably containing up to three carbon atoms.

Salts of the compounds of formula (I) include pharmaceutically acceptable salts and salts which may not be pharmaceutically acceptable but may be useful in the preparation of compounds of formula (I) and pharmaceutically acceptable salts thereof. Salts may be derived from certain inorganic or organic acids, or certain inorganic or organic bases.

The invention includes within its scope all possible stoichiometric and non-stoichiometric forms of the salts of the compounds of formula (I).

It is to be understood that references herein to compounds of the invention mean a compound of formula (I) as the free base, or as a salt, for example a pharmaceutically acceptable salt.

Salts of the compounds of formula (I) include pharmaceutically acceptable salts and salts which may not be pharmaceutically acceptable, but which may be useful in the preparation of compounds of formula and pharmaceutically acceptable salts thereof. Salts may be derived from certain inorganic or organic acids, or certain inorganic or organic bases.

The invention includes within its scope all possible stoichiometric and non-stoichiometric forms of the salts of the compounds of formula (I).

Examples of salts are pharmaceutically acceptable salts. Pharmaceutically acceptable salts include acid addition salts and base addition salts. For a review on suitable salts see "Berge et al., *J. Pharm. Sci*, 66:1-19 (1977)".

Examples of pharmaceutically acceptable acid addition salts of a compound of formula (I) include hydrobromide, hydrochloride, maleate, sulphate, p-toluenesulphonate, methanesulphonate, naphthalenesulphonate, and phenylsulphonate salts.

Salts may be formed using techniques well-known in the art, for example by precipitation or crystallisation from solution followed by filtration, or by evaporation of the solvent.

Typically, a pharmaceutically acceptable acid addition salt can be formed by reaction of a compound of formula (I) with a suitable strong acid (such as hydrobromic, hydrochloric, maleic, sulphuric, p-toluenesulphonic, methanesulphonic or naphthalenesulphonic acids), optionally in a suitable solvent such as an organic solvent, to give the salt which is usually isolated for example by crystallisation and filtration.

It will be appreciated that many organic compounds can form complexes with solvents in which they are reacted or from which they are precipitated or crystallised. These complexes are known as "solvates". For example, a complex with water is known as a "hydrate". Solvents with high boiling points and/or solvents with a high propensity to form hydrogen bonds such as water, ethanol, iso-propyl alcohol, and N-methylpyrrolidinone may be used to form solvates. Methods for the identification of solvated include, but are not limited to, NMR and microanalysis. Solvates of the compounds of formula (I) are within the scope of the invention. As used herein, the term solvate encompasses solvates of both a free base compound as well as any salt thereof.

Certain of the compounds of the invention may contain chiral atoms and/or multiple bonds, and hence may exist in one or more stereoisomeric forms. The present invention encompasses all of the stereoisomers of the compounds of the invention, including optical isomers, whether as individual stereoisomers or as mixtures thereof including racemic modifications. Any stereoisomer may contain less than 10% by weight, for example less than 5% by weight, or less than 0.5% by weight, of any other stereoisomer. For example, any optical isomer may contain less than 10% by weight, for example less than 5% by weight, or less than 0.5% by weight, of its antipode.

Certain of the compounds of the invention may exist in tautomeric forms. It will be understood that the present invention encompasses all of the tautomers of the compounds of the invention whether as individual tautomers or as mixtures thereof.

The compounds of the invention may be in crystalline or amorphous form. Furthermore, some of the crystalline forms of the compounds of the invention may exist as polymorphs, all of which are included within the scope of the present invention. The most thermodynamically stable polymorphic form or forms of the compounds of the invention are of particular interest.

Polymorphic forms of compounds of the invention may be characterised and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ssNMR).

It will be appreciated from the foregoing that included within the scope of the invention are solvates, hydrates, isomers and polymorphic forms of the compounds of formula (I) and salts and solvates thereof.

Examples of disease states in which the compounds of formula (I) and pharmaceutically acceptable salts thereof have potentially beneficial effects include allergic diseases and other inflammatory conditions for example allergic rhinitis and asthma, infectious diseases, and cancer. The compounds of formula (I) and pharmaceutically acceptable salts thereof are also of potential use as vaccine adjuvants.

As modulators of the immune response the compounds of formula (I) and pharmaceutically acceptable salts thereof may also be useful, as stand-alone or in combination as an adjuvant, in the treatment and/or prevention of immune-mediated disorders, including but not limited to inflammatory or allergic diseases such as asthma, allergic rhinitis and rhinoconjuctivitis, food allergy, hypersensitivity lung diseases, eosinophilic pneumonitis, delayed-type hypersensitivity disorders, atherosclerosis, pancreatitis, gastritis, colitis, osteoarthritis, psoriasis, sarcoidosis, pulmonary fibrosis, respiratory distress syndrome, bronchiolitis, chronic obstructive pulmonary disease, sinusitis, cystic fibrosis, actinic keratosis, skin dysplasia, chronic urticaria, eczema and all types of dermatitis.

The compounds of formula (I) and pharmaceutically acceptable salts thereof may also be useful in the treatment and/or prevention of reactions against respiratory infections, including but not limited to airways viral exacerbations and tonsillitis. The compounds may also be useful in the treatment and/or prevention of autoimmune diseases including but not limited to rheumatoid arthritis, psoriatic arthritis, systemic lupus erythematosus, Sjöegrens disease, ankylosing spondylitis, scleroderma, dermatomyositis, diabetes, graft rejection, including graft-versus-host disease, inflammatory bowel diseases including, but not limited to, Crohn's disease and ulcerative colitis.

The compounds of formula (I) and pharmaceutically acceptable salts thereof may also be useful in the treatment of infectious diseases including, but not limited to, those caused by hepatitis viruses (e.g. hepatitis B virus, hepatitis C virus), human immunodeficiency virus, papillomaviruses, herpesviruses, respiratory viruses (e.g. influenza viruses, respiratory syncytial virus, rhinovirus, metapneumovirus, parainfluenzavirus, SARS), and West Nile virus. The compounds of formula (I) and pharmaceutically acceptable salts thereof may also be useful in the treatment of microbial infections caused by, for example, bacteria, fungi, or protozoa. These include, but are not limited to, tuberculosis, bacterial pneumonia, aspergillosis, histoplasmosis, candidosis, pneumocystosis, leprosy, chlamydia, cryptococcal disease, cryptosporidosis, toxoplasmosis, leishmania, malaria, and trypanosomiasis.

The compounds of formula (I) and pharmaceutically acceptable salts thereof may also be useful in the treatment of various cancers, in particular the treatment of cancers that are known to be responsive to immunotherapy and including, but not limited to, renal cell carcinoma, lung cancer, breast cancer, colorectal cancer, bladder cancer, melanoma, leukaemia, lymphomas and ovarian cancer.

It will be appreciated by those skilled in the art that references herein to treatment or therapy may, depending on the condition, extend to prophylaxis as well as the treatment of established conditions.

As mentioned herein, compounds of formula (I) and pharmaceutically acceptable salts thereof may be useful as active therapeutic agents.

The compounds of formula (I) and pharmaceutically acceptable salts thereof may be formulated for administration in any convenient way.

The compounds of formula (I) and pharmaceutically acceptable salts thereof may, for example, be formulated for oral, topical, inhaled, intranasal, buccal, parenteral (for example intravenous, subcutaneous, intradermal, or intramuscular) or rectal administration. In one aspect, the compounds of formula (I) and pharmaceutically acceptable salts thereof are formulated for oral administration. In a further aspect, the compounds of formula (I) and pharmaceutically acceptable salts thereof are formulated for topical administration, for example intranasal or inhaled administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

Compositions for intranasal administration include aqueous compositions administered to the nose by drops or by pressurised pump. Suitable compositions contain water as the diluent or carrier for this purpose. Compositions for administration to the lung or nose may contain one or more excipients, for example one or more suspending agents, one or more preservatives, one or more surfactants, one or more tonicity adjusting agents, one or more co-solvents, and may include components to control the pH of the composition, for example a buffer system. Further, the compositions may contain other excipients such as antioxidants, for example sodium metabisulphite, and taste-masking agents. Compositions may also be administered to the nose or other regions of the respiratory tract by nebulisation.

Intranasal compositions may permit the compound(s) of formula (I) or (a) pharmaceutically acceptable salt(s) thereof to be delivered to all areas of the nasal cavities (the target tissue) and further, may permit the compound(s) of formula (I) or (a) pharmaceutically acceptable salt(s) thereof to remain in contact with the target tissue for longer periods of time. A suitable dosing regime for intranasal compositions would be for the patient to inhale slowly through the nose subsequent to the nasal cavity being cleared. During inhalation the composition would be administered to one nostril while the other is manually compressed. This procedure would then be repeated for the other nostril. Typically, one or two sprays per nostril would be administered by the above procedure one, two, or three times each day, ideally once daily. Of particular interest are intranasal compositions suitable for once-daily administration.

The suspending agent(s), if included, will typically be present in an amount of from 0.1 to 5% (w/w), such as from 1.5% to 2.4% (w/w), based on the total weight of the composition. Examples of pharmaceutically acceptable suspending agents include, but are not limited to, Avicel® (microcrystalline cellulose and carboxymethylcellulose sodium), carboxymethylcellulose sodium, veegum, tragacanth, bentonite, methylcellulose, xanthan gum, carbopol and polyethylene glycols.

Compositions for administration to the lung or nose may contain one or more excipients may be protected from microbial or fungal contamination and growth by inclusion of one or more preservatives. Examples of pharmaceutically acceptable anti-microbial agents or preservatives include, but are not limited to, quaternary ammonium compounds (for example benzalkonium chloride, benzethonium chloride, cetrimide, cetylpyridinium chloride, lauralkonium chloride and myristyl picolinium chloride), mercurial agents (for example phenylmercuric nitrate, phenylmercuric acetate and thimerosal), alcoholic agents (for example chlorobutanol, phenylethyl alcohol and benzyl alcohol), antibacterial esters (for example esters of para-hydroxybenzoic acid), chelating agents such as disodium edetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives include, but are not limited to, sodium benzoate, sorbic acid, sodium propionate, methylparaben, ethylparaben, propylparaben and butylparaben. The preservative(s), if included, may be present in an amount of from 0.001 to 1% (w/w), such as from 0.015% to 0.5% (w/w) based on the total weight of the composition.

Compositions (for example wherein at least one compound is in suspension) may include one or more surfactants which functions to facilitate dissolution of the medicament particles in the aqueous phase of the composition. For example, the amount of surfactant used is an amount which will not cause foaming during mixing. Examples of pharmaceutically acceptable surfactants include fatty alcohols, esters and ethers, such as polyoxyethylene (20) sorbitan monooleate (Polysorbate 80), macrogol ethers, and poloxamers. The surfactant may be present in an amount of between about 0.01 to 10% (w/w), such as from 0.01 to 0.75% (w/w), for example about 0.5% (w/w), based on the total weight of the composition.

One or more tonicity-adjusting agent(s) may be included to achieve tonicity with body fluids e.g. fluids of the nasal cavity, resulting in reduced levels of irritancy. Examples of pharmaceutically acceptable tonicity-adjusting agents include, but are not limited to, sodium chloride, dextrose, xylitol, calcium chloride, glucose, glycerine and sorbitol. A tonicity-adjusting agent, if present, may be included in an amount of from 0.1 to 10% (w/w), such as from 4.5 to 5.5% (w/w), for example about 5.0% (w/w), based on the total weight of the composition.

The compositions of the invention may be buffered by the addition of suitable buffering agents such as sodium citrate, citric acid, trometamol, phosphates such as disodium phosphate (for example the dodecahydrate, heptahydrate, dihydrate and anhydrous forms), or sodium phosphate and mixtures thereof.

A buffering agent, if present, may be included in an amount of from 0.1 to 5% (w/w), for example 1 to 3% (w/w) based on the total weight of the composition.

Examples of taste-masking agents include sucralose, sucrose, saccharin or a salt thereof, fructose, dextrose, glycerol, corn syrup, aspartame, acesulfame-K, xylitol, sorbitol, erythritol, ammonium glycyrrhizinate, thaumatin, neotame, mannitol, menthol, eucalyptus oil, camphor, a natural flavouring agent, an artificial flavouring agent, and combinations thereof.

One or more co-solvent(s) may be included to aid solubility of the medicament compound(s) and/or other excipients. Examples of pharmaceutically acceptable co-solvents include, but are not limited to, propylene glycol, dipropylene glycol, ethylene glycol, glycerol, ethanol, polyethylene glycols (for example PEG300 or PEG400), and methanol. In one embodiment, the co-solvent is propylene glycol.

Co-solvent(s), if present, may be included in an amount of from 0.05 to 30% (w/w), such as from 1 to 25% (w/w), for example from 1 to 10% (w/w) based on the total weight of the composition.

Compositions for inhaled administration include aqueous, organic or aqueous/organic mixtures, dry powder or crystalline compositions administered to the respiratory tract by pressurised pump or inhaler, for example, reservoir dry powder inhalers, unit-dose dry powder inhalers, pre-metered multi-dose dry powder inhalers, nasal inhalers or pressurised aerosol inhalers, nebulisers or insufflators. Suitable compositions contain water as the diluent or carrier for this purpose and may be provided with conventional excipients such as buffering agents, tonicity modifying agents and the like. Aqueous compositions may also be administered to the nose and other regions of the respiratory tract by nebulisation. Such compositions may be aqueous solutions or suspensions or aerosols delivered from pressurised packs, such as a metered dose inhaler, with the use of a suitable liquefied propellant.

Compositions for administration topically to the nose (for example, for the treatment of rhinitis) or to the lung, include pressurised aerosol compositions and aqueous compositions delivered to the nasal cavities by pressurised pump. Compositions which are non-pressurised and are suitable for administration topically to the nasal cavity are of particular interest. Suitable compositions contain water as the diluent or carrier for this purpose. Aqueous compositions for administration to the lung or nose may be provided with conventional excipients such as buffering agents, tonicity-modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity. A fluid dispenser of the aforementioned type is described and illustrated in International Patent Application publication number WO 2005/044354 (Glaxo Group Limited). The dispenser has a housing which houses a fluid-discharge device having a compression pump mounted on a container for containing a fluid composition. The housing has at least one finger-operable side lever which is movable inwardly with respect to the housing to move the container upwardly in the housing by means of a cam to cause the pump to compress and pump a metered dose of the composition out of a pump stem through a nasal nozzle of the housing. In one embodiment, the fluid dispenser is of the general type illustrated in FIGS. 30-40 of WO 2005/044354.

Aqueous compositions containing a compound of formula (I) or a pharmaceutically acceptable salt thereof may also be delivered by a pump as disclosed in International Patent Application publication number WO2007/138084 (Glaxo Group Limited), for example as disclosed with reference to FIGS. 22-46 thereof, or as disclosed in United Kingdom patent application number GB0723418.0 (Glaxo Group Limited), for example as disclosed with reference to FIGS. 7-32 thereof. The pump may be actuated by an actuator as disclosed in FIGS. 1-6 of GB0723418.0.

Dry powder compositions for topical delivery to the lung by inhalation may, for example, be presented in capsules and cartridges of for example gelatine, or blisters of for example laminated aluminium foil, for use in an inhaler or insufflator. Powder blend compositions generally contain a powder mix for inhalation of the compound of formula (I) or a pharmaceutically acceptable salt thereof and a suitable powder base (carrier/diluent/excipient substance) such as mono-, di-, or polysaccharides (for example lactose or starch). Dry powder compositions may also include, in addition to the drug and carrier, a further excipient (for example a ternary agent such as a sugar ester for example cellobiose octaacetate, calcium stearate, or magnesium stearate.

In one embodiment, a composition suitable for inhaled administration may be incorporated into a plurality of sealed dose containers provided on medicament pack(s) mounted inside a suitable inhalation device. The containers may be rupturable, peelable, or otherwise openable one-at-a-time and the doses of the dry powder composition administered by inhalation on a mouthpiece of the inhalation device, as known in the art. The medicament pack may take a number of different forms, for instance a disk-shape or an elongate strip. Representative inhalation devices are the DISKHALER™ and DISKUS™ devices, marketed by GlaxoSmithKline.

A dry powder inhalable composition may also be provided as a bulk reservoir in an inhalation device, the device then being provided with a metering mechanism for metering a dose of the composition from the reservoir to an inhalation channel where the metered dose is able to be inhaled by a patient inhaling at a mouthpiece of the device. Exemplary marketed devices of this type are TURBUHALER™ (AstraZeneca), TWISTHALER™ (Schering) and CLICKHALER™ (Innovata.)

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ (GlaxoSmithKline) and HANDIHALER™ (Boehringer Ingelheim.)

Pressurised aerosol compositions suitable for inhalation can be either a suspension or a solution and may contain a compound of formula (I) or a pharmaceutically acceptable salt thereof and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional composition excipients well known in the art such as surfactants e.g. oleic acid, lecithin or an oligolactic acid or derivative thereof e.g. as described in WO 94/21229 and WO 98/34596 (Minnesota Mining and Manufacturing Company) and co-solvents e.g. ethanol. Pressurised compositions will generally be retained in a canister (e.g. an aluminium canister) closed with a valve (e.g. a metering valve) and fitted into an actuator provided with a mouthpiece.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, wool-fat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

The compounds of formula (I) and pharmaceutically acceptable salts thereof may, for example, be formulated for transdermal delivery by composition into patches or other devices (e.g. pressurised gas devices) which deliver the active component into the skin.

For buccal administration the compositions may take the form of tablets or lozenges formulated in the conventional manner.

The compounds of formula (I) and pharmaceutically acceptable salts thereof may also be formulated as suppositories, e.g. containing conventional suppository bases such as cocoa butter or other glycerides.

The compounds of formula (I) and pharmaceutically acceptable salts thereof may also be formulated for parenteral administration by bolus injection or continuous infusion and may be presented in unit dose form, for instance as ampoules, vials, small volume infusions or pre-filled syringes, or in multidose containers with an added preservative. The compositions may take such forms as solutions, suspensions, or emulsions in aqueous or non-aqueous vehicles, and may contain formulatory agents such as anti-oxidants, buffers, anti-microbial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

The compounds of formula (I) and pharmaceutically acceptable salts thereof may also be formulated with vaccines as adjuvants to modulate their activity. Such compositions may contain antibody(ies) or antibody fragment(s) or an antigenic component including but not limited to protein, DNA, live or dead bacteria and/or viruses or virus-like particles, together with one or more components with adjuvant activity including but not limited to aluminium salts, oil and water emulsions, heat shock proteins, lipid A preparations and derivatives, glycolipids, other TLR agonists such as CpG DNA or similar agents, cytokines such as GM-CSF or IL-12 or similar agents.

The compounds of formula (I) and pharmaceutically acceptable salts thereof may be employed alone or in combination with other therapeutic agents. The compounds of formula (I) and pharmaceutically acceptable salts thereof and the other pharmaceutically active agent(s) may be administered together or separately and, when administered separately, administration may occur simultaneously or sequentially, in any order. The amounts of the compound(s) of formula (I) or (a) pharmaceutically acceptable salt(s) thereof and the other pharmaceutically active agent(s) and the relative timings of administration will be selected in order to achieve the desired combined therapeutic effect. The administration of a combination of a compound of formula (I) or a pharmaceutically acceptable salt thereof with other treatment agents may be by administration concomitantly in a unitary pharmaceutical composition including both compounds, or in separate pharmaceutical compositions each including one of the compounds. Alternatively, the combination may be administered separately in a sequential manner wherein one treatment agent is administered first and the other second or vice versa. Such sequential administration may be close in time or remote in time.

The compounds of formula (I) and pharmaceutically acceptable salts thereof may be used in combination with one or more agents useful in the prevention or treatment of viral infections. Examples of such agents include, without limitation; polymerase inhibitors such as those disclosed in WO 2004/037818-A1, as well as those disclosed in WO 2004/037818 and WO 2006/045613; JTK-003, JTK-019, NM-283, HCV-796, R-803, R1728, R1626, as well as those disclosed in WO 2006/018725, WO 2004/074270, WO 2003/095441, US2005/0176701, WO 2006/020082, WO 2005/080388, WO 2004/064925, WO 2004/065367, WO 2003/007945, WO 02/04425, WO 2005/014543, WO 2003/000254, EP 1065213, WO 01/47883, WO 2002/057287, WO 2002/057245 and similar agents; replication inhibitors such as acyclovir, famciclovir, ganciclovir, cidofovir, lamivudine and similar agents; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034; and similar agents; nucleoside and nucleotide reverse transcriptase inhibitors such as zidovudine, didanosine, lamivudine, zalcitabine, abacavir, stavidine, adefovir, adefovir dipivoxil, fozivudine, todoxil, emtricitabine, alovudine, amdoxovir, elvucitabine, and similar agents; non-nucleoside reverse transcriptase inhibitors (including an agent having anti-oxidation activity such as immunocal, oltipraz etc.) such as nevirapine, delavirdine, efavirenz, loviride, immunocal, oltipraz, capravirine, TMC-278, TMC-125, etravirine, and similar agents; entry inhibitors such as enfuvirtide (T-20), T-1249, PRO-542, PRO-140, TNX-355, BMS-806, 5-Helix and similar agents; integrase inhibitors such as L-870, 180 and similar agents; budding inhibitors such as PA-344 and PA-457, and similar agents; chemokine receptor inhibitors such as vicriviroc (Sch-C), Sch-D, TAK779, maraviroc (UK-427,857), TAK449, as well as those disclosed in WO 02/74769, WO 2004/054974, WO 2004/055012, WO 2004/055010, WO 2004/055016, WO 2004/055011, and WO 2004/054581, and similar agents; neuraminidase inhibitors such as CS-8958, zanamivir, oseltamivir, peramivir and similar agents; ion channel blockers such as amantadine or rimantadine and similar agents; and interfering RNA and antisense oligonucleotides and such as ISIS-14803 and similar agents; antiviral agents of undetermined mechanism of action, for example those disclosed in WO 2005/105761, WO 2003/085375, WO 2006/122011, ribavirin, and similar agents. The compounds of formula (I) and pharmaceutically acceptable salts thereof may also be used in combination with one or more other agents which may be useful in the prevention or treatment of viral infections for example immune therapies (e.g. interferon or other cytokines/chemokines, cytokine/chemokine receptor modulators, cytokine agonists or antagonists and similar agents); and therapeutic vaccines, antifibrotic agents, anti-inflammatory agents such as corticosteroids or NSAIDs (non-steroidal anti-inflammatory agents) and similar agents.

The compounds of formula (I) and pharmaceutically acceptable salts thereof may be used in combination with one or more other agents which may be useful in the prevention or treatment of allergic disease, inflammatory disease, autoimmune disease, for example; antigen immunotherapy, antihistamines, steroids, NSAIDs, bronchodilators (e.g. beta 2 agonists, adrenergic agonists, anticholinergic agents, theophylline), methotrexate, leukotriene modulators and similar agents; monoclonal antibody therapy such as anti-IgE, anti-TNF, anti-IL-5, anti-IL-6, anti-IL-12, anti-IL-1 and similar agents; receptor therapies e.g. entanercept and similar agents; antigen non-specific immunotherapies (e.g. interferon or other cytokines/chemokines, cytokine/chemokine receptor modulators, cytokine agonists or antagonists, TLR agonists and similar agents).

The compounds of formula (I) and pharmaceutically acceptable salts thereof may be used in combination with one or more other agents which may be useful in the prevention or treatment of cancer, for example chemotherapeutics such as alkylating agents, topoisomerase inhibitors, antimetabolites, antimitotic agents, kinase inhibitors and similar agents; monoclonal antibody therapy such as trastuzumab, gemtuzumab and other similar agents; and hormone therapy such as tamoxifen, goserelin and similar agents.

The pharmaceutical compositions according to the invention may also be used alone or in combination with at least one other therapeutic agent in other therapeutic areas, for example gastrointestinal disease. The compositions according to the invention may also be used in combination with gene replacement therapy.

The invention includes in a further aspect a combination comprising a compound of formula (I), or a pharmaceutically acceptable salt thereof, together with at least one other therapeutically active agent.

The combinations referred to above may conveniently be presented for use in the form of a pharmaceutical composition and thus pharmaceutical compositions comprising a combination as defined above together with at least one pharmaceutically acceptable diluent or carrier thereof represent a further aspect of the invention.

A therapeutically effective amount of a compound of formula (I) or a pharmaceutically acceptable salt thereof will depend upon a number of factors. For example, the species, age, and weight of the recipient, the precise condition requiring treatment and its severity, the nature of the composition, and the route of administration are all factors to be considered. The therapeutically effective amount ultimately should be at the discretion of the attendant physician. Regardless, an effective amount of a compound of the present invention for the treatment of humans suffering from frailty, generally, should be in the range of 0.0001 to 100 mg/kg body weight of recipient per day. More usually the effective amount should be in the range of 0.001 to 10 mg/kg body weight per day. Thus, for a 70 kg adult one example of an actual amount per day would usually be from 7 to 700 mg. For intranasal and inhaled routes of administration, typical doses for a 70 kg adult should be in the range of 1 mg to 1 mg per day. This amount may be given in a single dose per day or in a number (such as two, three, four, five, or more) of sub-doses per day such that the total daily dose is the same. An effective amount of a pharmaceutically acceptable salt of a compound of formula (I) may be determined as a proportion of the effective amount of the compound of formula (I) or a pharmaceutically acceptable salt thereof per se. Similar dosages should be appropriate for treatment of the other conditions referred to herein.

Compounds of formula (I) and pharmaceutically acceptable salts thereof may also be administered at any appropriate frequency e.g. 1-7 times per week. The precise dosing regimen will of course depend on factors such as the therapeutic indication, the age and condition of the patient, and the particular route of administration chosen.

Pharmaceutical compositions may be presented in unit-dose forms containing a predetermined amount of active ingredient per unit dose. Such a unit may contain, as a non-limiting example, 0.5 mg to 1 g of a compound of formula (I) or a pharmaceutically acceptable salt thereof, depending on the condition being treated, the route of administration, and the age, weight, and condition of the patient. Preferred unit-dosage compositions are those containing a daily dose or sub-dose, as herein above recited, or an appropriate fraction thereof, of an active ingredient. Such pharmaceutical compositions may be prepared by any of the methods well-known in the pharmacy art.

There, is thus further provided a pharmaceutical composition comprising a compound of formula (I), or a pharmaceutically acceptable salt thereof, and one or more pharmaceutically acceptable diluents or carriers.

There is also provided a process for preparing such a pharmaceutical composition which comprises admixing a compound of formula (I), or a pharmaceutically acceptable salt thereof, with one or more pharmaceutically acceptable diluents or carriers.

The compounds of formula (I) and salts thereof may be prepared by the methodology described hereinafter, constituting further aspects of this invention.

Accordingly, there is provided a process, Process A, for the preparation of a compound of formula (I), in which Y is carbon, which process comprises the reaction of a compound of formula (IIA)

(IIA)

with a compound of formula (IIIA)

(IIIA)

wherein $R^1$, n, X and Y are as hereinbefore defined for a compound of formula (I), and thereafter, removing the methyl protecting group (OMe), and thereafter, if required, carrying out one or more of the following optional steps:

(i). converting a compound of formula (I) to a further compound of formula (I);

(ii). removing any necessary further protecting group;

(iii). preparing a salt or solvate of the compound so-formed.

For example, a compound of Formula (IIA) may be dissolved in a suitable solvent, such as N,N'-dimethylformamide (DMF) and added to a solution of a compound of formula (IIIA), which may be introduced neat or dissolved in a suitable solvent such as acetonitrile, in the presence of a suitable base, such as di-isopropylethylamine (DIPEA). The reaction mixture may optionally be heated to a suitable elevated temperature, such as from 45 to 55° C., for a suitable length of time, such as overnight, until the reaction has reached completion.

Removal of the methyl protecting group (OMe in the compound of formula (IIA)) may be achieved by treating the resulting compound with a suitable strength (e.g. 4N or 2N) solution of hydrogen chloride in a suitable solvent, for example 1,4-dioxane, typically at room temperature for an appropriate length of time such as from 4 hours to 24 hours.

Compounds of formula (IIA) may be prepared according to Scheme 1 below.

Compounds of formula (IIIA) are commercially available, and include 2-bromoethanol.

Scheme 1:
Preparation of compounds of Formula (IIA) in which Y is carbon

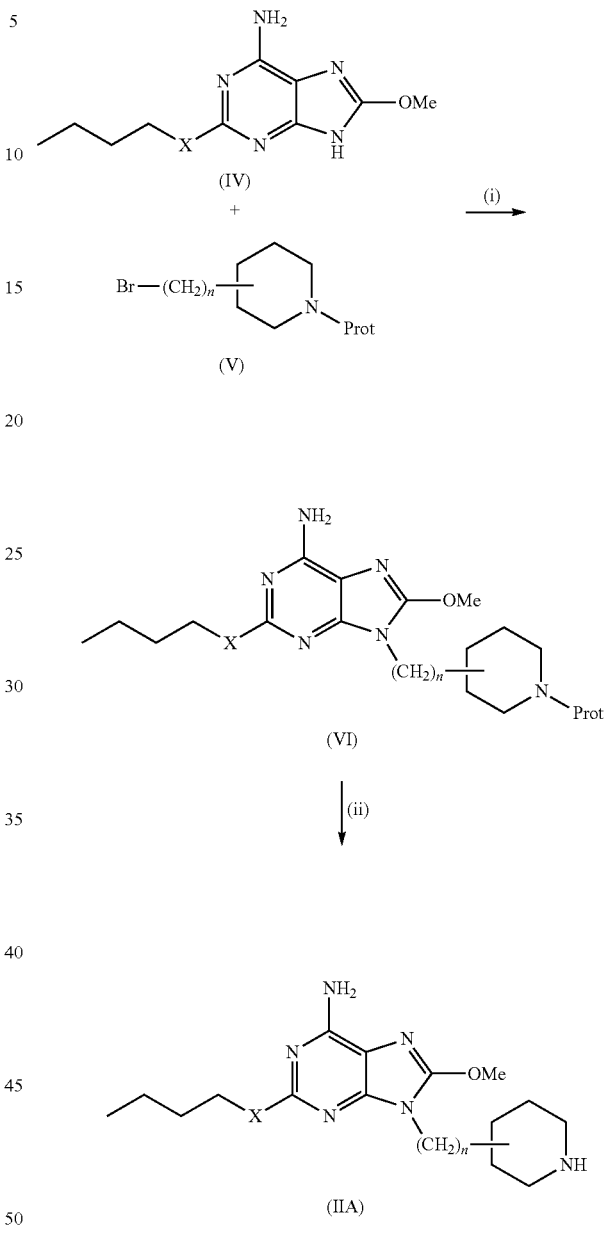

wherein $R^1$, n and X are as hereinbefore defined for a compound of formula (I) and Prot is a suitable protecting group, usually CBZ (carbobenzyloxy).

Reagents and Conditions: (i) suitable solvent such as DMF, suitable base such as potassium carbonate, usually at an elevated temperature such as from 50 to 60° C., for a suitable length of time such as 18 to 24 hours; (ii) Deprotection. When Prot=CBZ, the CBZ group may be removed by reduction in the presence of 10% palladium on carbon in a suitable solvent such as ethanol.

Compounds of formula (IV) may be prepared according to Scheme 2 and Scheme 3 below.

Compounds of formula (V) may be prepared according to Scheme 4 below.

Scheme 2: Preparation of compound of formula (IV) in which X is oxygen (IVA)

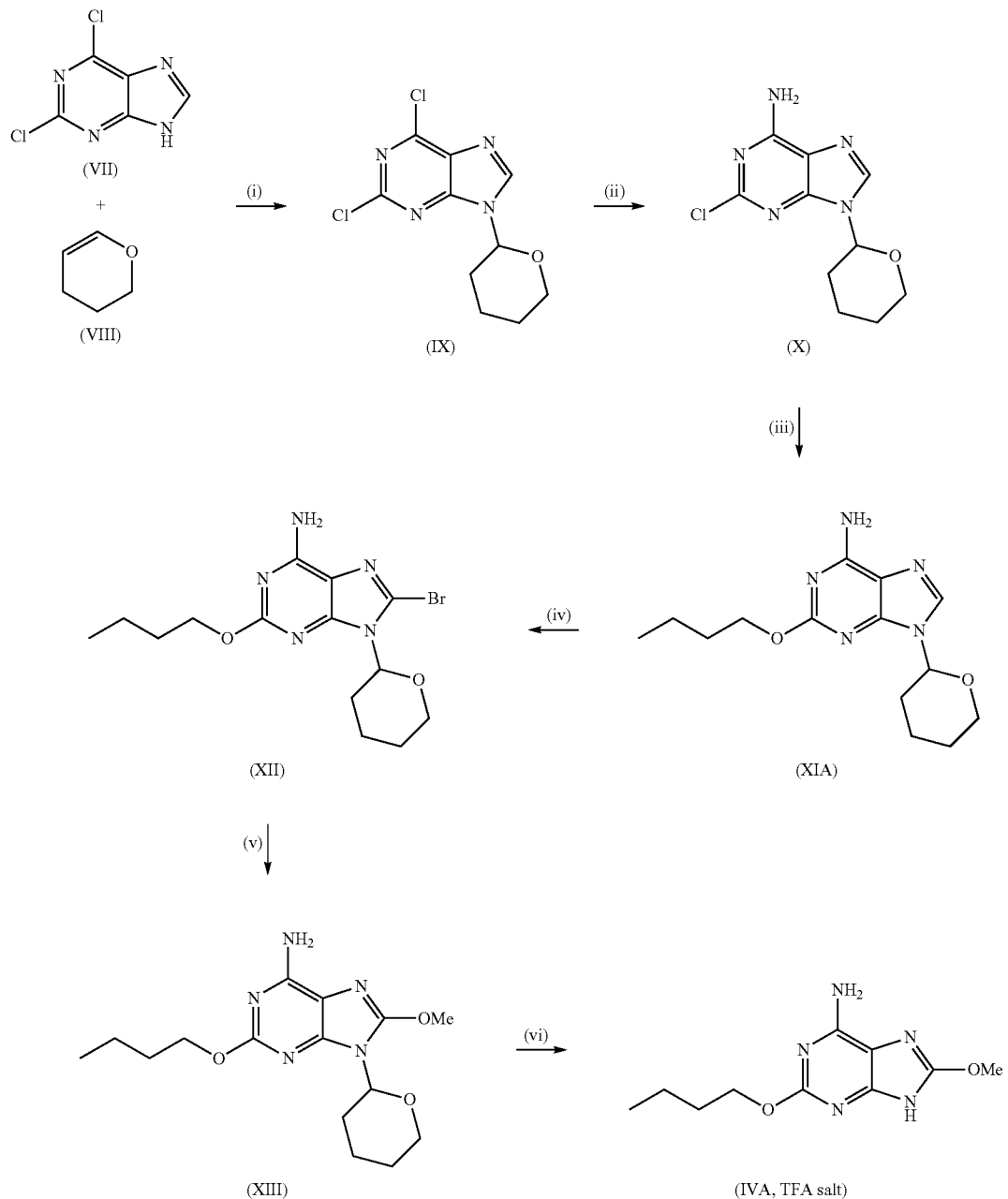

wherein TFA is trifluoroacetic acid.

Reagents and Conditions: (i) suitable solvent, such as ethyl acetate in the presence of a suitable acid such as p-toluene sulfonic acid, usually at an elevated temperature such as from 45 to 55° C. for a suitable period of time such as approximately an hour; (ii) suitable solvent such as isopropylalcohol, ammonia, usually at an elevated temperature such as from 45 to 55° C. for a suitable period of time such as from 5 to 24 hours; (iii) suitable base such as sodium tert-butoxide, n-butanol (commercially available, for example, from Aldrich), usually at an elevated temperature such as approximately 100° C. for a suitable period of time such as from 18 to 24 hours; (iv) suitable solvent such as chloroform, N-bromosuccinimide (commercially available, for example, from Aldrich), at a suitable lowered temperature such as 0° C. (in an ice bath), then raising to ambient temperature for a suitable period of time such as from 5 to 7 hours; (v) sodium methoxide/methanol as a suitable base and solvent combination, usually at reflux for a suitable period of time such as from 4 to 6 hours; (vi) suitable solvent such as methanol, suitable acid such as trifluoroacetic acid, for a suitable period of time such as from 36 to 60 hours.

Compounds of formulas (VII) and (VIII) are commercially available.

Compounds of formula (IX), (X), (XIA), (XII), (XIII) and (IV) may also be prepared according to the methods disclosed in International Patent Application Publication Number WO2008/101867.

Compounds of formula (X) may also be made directly from compounds of formula (VII) and (VIII) without isolation of the intermediate of formula (IX).

Scheme 3: Preparation of compound of formula (IV) in which X is nitrogen (IVB)

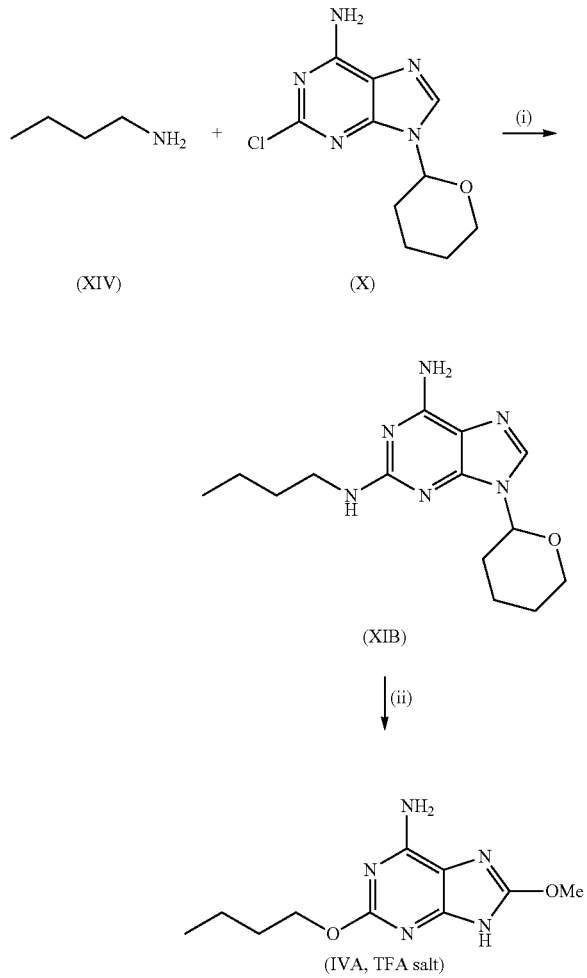

wherein TFA is trifluoroacetic acid.

Reagents and Conditions: (i) suitable solvent, such as ethylene glycol, usually at an elevated temperature such as from 110 to 130° C., for a suitable period of time such as from 12 to 24 hours; (ii) suitable solvent such as chloroform, N-bromosuccinimide (commercially available, for example, from Aldrich), at ambient temperature for a suitable period of time such as from 15 to 35 minutes, then sodium methoxide/methanol as a suitable base and solvent combination, usually at an elevated temperature such as from 60 to 70° C., for a suitable period of time such as from 12 to 24 hours followed by a suitable solvent such as methanol, suitable acid such as trifluoroacetic acid, for a suitable period of time such as from 36 to 60 hours.

The compound of formula (XIV) is commercially available.

The compound of formula (X) is prepared as above in Scheme 2.

Scheme 4: Preparation of compounds of formula (V) in which Y is carbon

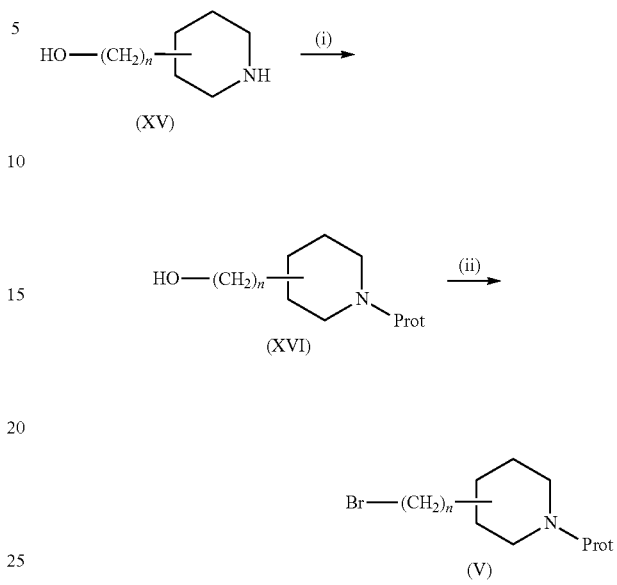

wherein n is as hereinbefore defined for a compound of formula (I) and Prot is a suitable protecting group, usually CBZ.

It will be appreciated that in compounds of formula (XV), the (CH$_2$), group may not be connected to the nitrogen of the six membered ring.

Reagents and Conditions: (i) either benzyl chloroformate (commercially available, for example, from Aldrich), in the presence of a suitable base such as triethylamine, in a suitable solvent such as acetonitrile, usually at a suitable lowered temperature such as 0° C. (in an ice bath), then raising to ambient temperature for a suitable period of time such as from 12 to 24 hours; or using 1-({[(phenylmethyl)oxy]carbonyl}oxy)-2,5-pyrrolidinedione (commercially available, for example, from Aldrich), in the presence of a suitable base such as triethylamine, in a suitable solvent such as dichloromethane at ambient temperature for a suitable period of time such as from 12 to 24 hours.

Compounds of formula (XV) may also be made from the corresponding acid (instead of the alcohol):

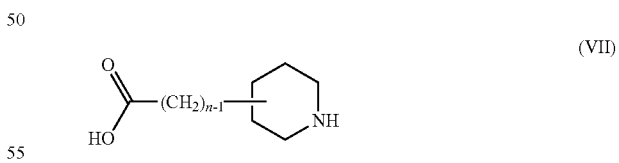

by reduction using a suitable solvent such as tetrahydrofuran, in the presence of borane-tetrahydrofuran complex, usually at a lowered temperature such as at 0° C. (in an ice bath). The reaction is usually quenched using as suitable solvent such as methanol and then further with a suitable acid, such as 2N hydrogen chloride in methanol.

There is also provided a process, Process B, for the preparation of a compound of formula (I), in which Y is nitrogen and (CH$_2$)$_n$ is connected through Y, which process comprises the deprotection of a compound of formula (IIB):

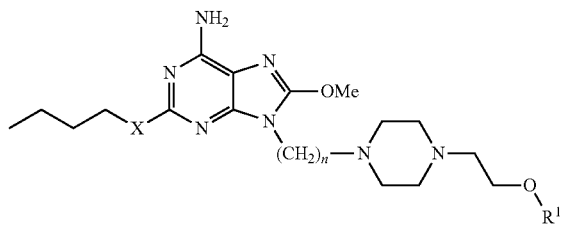

(IIB)

wherein $R^1$, n and X are as hereinbefore defined for a compound of formula (I), and thereafter, if required, carrying out one or more of the following optional steps:

(i) converting a compound of formula (I) to a further compound of formula (I);

(ii) preparing a salt or solvate of the compound so-formed.

For example, a compound of formula (IIB) is dissolved in a suitable solvent, for example methanol, and treated with 4N solution of hydrogen chloride in a suitable solvent, for example 1,4-dioxane. The reaction is stirred at a suitable temperature such as at ambient temperature, for a suitable period of time such as 4 to 24 hours.

Compounds of formula (IIB) may be prepared according to Scheme 5 below.

Scheme 5: Preparation of compounds of formula (IIB), in which Y is nitrogen and $(CH_2)_n$ is connected through Y

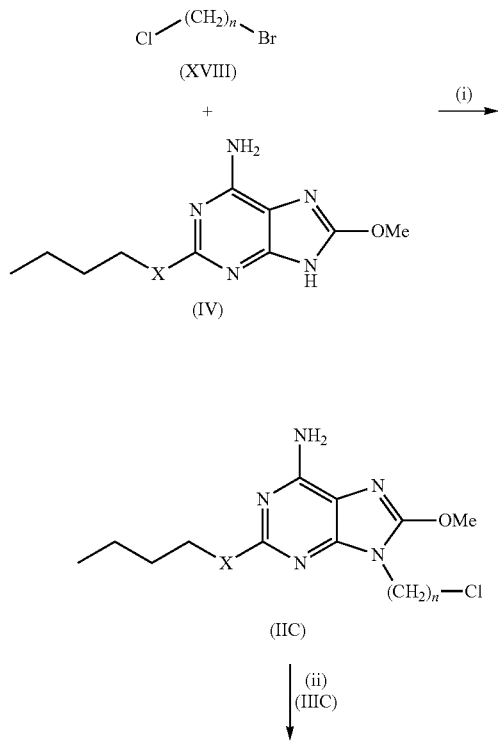

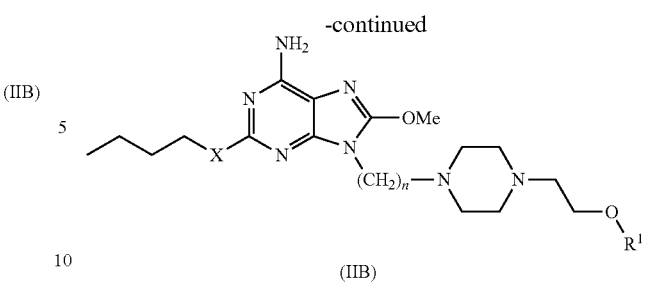

(IIB)

wherein n, X and $R^1$ are as hereinbefore defined for a compound of formula (I).

Reagents and Conditions: (i) compound (IV) is dissolved in a suitable solvent such as DMF in the presence of a suitable base such as potassium carbonate, usually at an elevated temperature such as from 40 to 60° C., for a suitable period of time such as from 0.5 to 2 hours, then cooling to a lowered temperature such as from 0° C. to ambient temperature and adding the compound of formula (XVIII) and reacting for a suitable period of time such as from 5 to 20 hours, (ii) compound of formula (IIIC), suitable solvent such as acetonitrile or DMF, suitable base such as DIPEA usually at an elevated temperature such as from 60 to 80° C., for a suitable period of time such as from 18 to 36 hours.

It will be appreciated that conversion of compounds of formula (IIC) to compounds of formula (I) may be carried out without isolation of compounds of formula (IIB).

Examples of other protecting groups that may be employed in the synthetic routes described herein and the means for their removal can be found in T. W. Greene '*Protective Groups in Organic Synthesis*,' 3rd edition, J. Wiley and Sons, 1999, incorporated herein by reference as it relates to such procedures.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with magnesium sulphate, or sodium sulphate, or passing through a hydrophobic frit, may be employed. Conventional methods of purification, for example crystallisation and chromatography, for example silica chromatography or reverse-phase chromatography, may be used as required. It will be appreciated that specific reaction times temperatures may typically be determined by reaction-monitoring techniques, for example thin-layer chromatography and LC-MS.

Where appropriate individual isomeric forms of the compounds of formula (I) may be prepared as individual isomers using conventional procedures such as the fractional crystallisation of diastereoisomeric derivatives or chiral high performance liquid chromatography (chiral HPLC). The invention is illustrated by reference to, but is in no way limited by, the following Examples.

Experimental Details

Experimental details of LCMS systems A-D as referred to herein are as follows:

System A

Column: 50 mm×2.1 mm ID, 1.7 μm Acquity HPLC BEH $C_{18}$

Flow Rate: 1 mL/min.

Temp: 40° C.

UV Detection Range: 210 to 350 nm

Mass spectrum: recorded on a mass spectrometer using alternative-scan positive and negative mode electrospray ionisation Solvents:
   A: 0.1% v/v formic acid in water
   B: 0.1% v/v formic acid acetonitrile Gradient:

| Time (min.) | A % | B % |
|---|---|---|
| 0 | 97 | 3 |
| 1.5 | 0 | 100 |
| 1.9 | 0 | 100 |
| 2.0 | 97 | 3 |

System B
Column: 30 mm×4.6 mm ID, 3.5 μm Sunfire $C_{18}$ column
Flow Rate: 3 mL/min.
Temp: 30° C.
UV Detection Range: 210 to 350 nm
Mass spectrum: recorded on a mass spectrometer using alternative-scan positive and negative mode electrospray ionisation Solvents:
   A: 0.1% v/v solution of formic acid in water
   B: 0.1% v/v solution of formic acid in acetonitrile Gradient:

| Time (min.) | A % | B % |
|---|---|---|
| 0 | 97 | 3 |
| 0.1 | 97 | 3 |
| 4.2 | 0 | 100 |
| 4.8 | 0 | 100 |
| 4.9 | 97 | 3 |
| 5.0 | 97 | 3 |

System C
Column: 50 mm×2.1 mm ID, 1.7 μm Acquity HPLC BEH $C_{18}$
Flow Rate: 1 mL/min.
Temp: 40° C.
UV Detection Range: 210 to 350 nm
Mass spectrum: recorded on a mass spectrometer using alternative-scan positive and negative mode electrospray ionisation Solvents:
   A: 10 mM Ammonium bicarbonate in water adjusted to pH10 with ammonia solution
   B: Acetonitrile Gradient:

| Time (min.) | A % | B % |
|---|---|---|
| 0 | 99 | 1 |
| 1.5 | 3 | 97 |
| 1.9 | 3 | 97 |
| 2.0 | 0 | 100 |

System D
Column: 50 mm×4.6 mm ID, XBridge $C_{18}$ column
Flow Rate: 3 mL/min.
Temp: 30° C.
UV Detection Range: 210 to 350 nm
Mass spectrum: recorded on a mass spectrometer using alternative-scan positive and negative mode electrospray ionisation Solvents:
   A: 10 mM Ammonium bicarbonate in water adjusted to pH10 with ammonia solution
   B: Acetonitrile Gradient:

| Time (min.) | A % | B % |
|---|---|---|
| 0 | 99 | 1 |
| 0.1 | 99 | 1 |
| 4.0 | 3 | 97 |
| 5.0 | 3 | 97 |

System E
Column: 30 mm×4.6 mm ID, Sunfire $C_{18}$ column
Flow Rate: 3 mL/min.
Temp: 30° C.
UV Detection Range: 210 to 350 nm
Mass spectrum: recorded on a mass spectrometer using alternative-scan positive and negative mode electrospray ionisation Solvents:
   A: 0.1% v/v solution of Trifluoracetic acid in water
   B: 0.1% v/v solution of Trifluoracetic acid in acetonitrile Gradient:

| Time (min.) | A % | B % |
|---|---|---|
| 0 | 97 | 3 |
| 0.1 | 97 | 3 |
| 4.2 | 0 | 100 |
| 4.8 | 0 | 100 |
| 4.9 | 97 | 3 |
| 5.0 | 97 | 3 |

Chromatographic purification was typically performed using pre-packed silica gel cartridges. The Flashmaster II is an automated multi-user flash chromatography system, available from Argonaut Technologies Ltd, which utilises disposable, normal phase, Solid Phase Extraction (SPE) cartridges (2 g to 100 g). It provides quaternary on-line solvent mixing to enable gradient methods to be run. Samples are queued using the multi-functional open access software, which manages solvents, flow-rates, gradient profile and collection conditions. The system is equipped with a Knauer variable wavelength UV-detector and two Gilson FC204 fraction-collectors enabling automated peak cutting, collection and tracking.

Solvent removal using a stream of nitrogen was performed at 30-40° C. on a GreenHouse Blowdown system available from Radleys Discovery Technologies Saffron Walden, Essex, CB11 3AZ. UK $^1$H NMR spectra were recorded in either $CDCl_3$ or DMSO-$d_6$ on either a Bruker DPX 400 or Bruker Avance DRX or Varian Unity 400 spectrometer all working at 400 MHz. The internal standard used was either tetramethylsilane or the residual protonated solvent at 7.25 ppm for $CDCl_3$ or 2.50 ppm for DMSO-$d_6$.

Mass directed autopreparative (MPAP) HPLC was undertaken under the conditions given below. The UV detection was an averaged signal from wavelength of 210 nm to 350 nm and mass spectra were recorded on a mass spectrometer using alternate-scan positive and negative mode electrospray ionization.

Method A:

Method A was conducted on an XBridge C$_{18}$ column (typically 150 mm×19 mm i.d. 5 μm packing diameter) at ambient temperature. The solvents employed were:
A=10 mM aqueous ammonium bicarbonate adjusted to pH 10 with ammonia solution.
B=acetonitrile.
Method B:

Method B was conducted on an Atlantis C$_{18}$ column (typically 100 mm×30 mm i.d. 5 μm packing diameter) at ambient temperature. The solvents employed were:
A=0.1% v/v solution of Formic acid in water
B=0.1% v/v solution of Formic acid in Acetonitrile.

Intermediates

Intermediate 1

2,6-Dichloro-9-(tetrahydro-2H-pyran-2-yl)-9H-purine

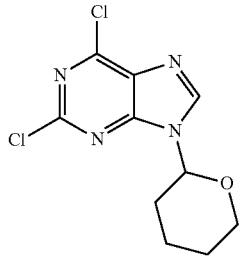 [SMILES: Clc1nc(Cl)c2ncn(C3CCCCO3)c2n1]

To 2,6-dichloropurine (commercially available, for example, from Aldrich) (25.0 g) was added ethyl acetate (260 mL), followed by p-toluenesulfonic acid (0.253 g). The mixture was heated to 50° C. and then 3,4-dihydro-2H-pyran (commercially available, for example, from Aldrich) (16.8 g) was added. The reaction mixture was then heated at 50° C. for 4 hours. The reaction mixture was evaporated in vacuo to give the title compound as a yellow solid (36.9 g).

$^1$H NMR (CDCl$_3$): 8.35 (1H, s), 5.77 (1H, dd), 4.20 (1H, m), 3.79 (1H, m), 2.20-1.65 (6H, m).

Intermediate 2

2-Chloro-9-(tetrahydro-2H-pyran-2-yl)-9H-purin-6-amine

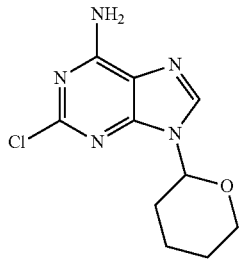 [SMILES: Nc1nc(Cl)nc2c1ncn2C1CCCCO1]

Preparation 1

2,6-Dichloro-9-(tetrahydro-2H-pyran-2-yl)-9H-purine (for example, as prepared for Intermediate 1) (36.9 g) was heated with 2M ammonia in isopropanol (250 mL) at 50° C. for 5 hours. After standing at ambient temperature overnight, a further quantity of 2M ammonia in isopropanol (100 mL) was added to break up the resultant cake and the reaction mixture was heated for a further 9 hours until the reaction was complete. To the reaction mixture was added water (70 mL) and the yellow solid filtered off. The solid was washed with isopropyl alcohol:water (5:1 (v/v), 60 mL) and then air-dried under suction to give a first crop. The filtrate was re-filtered after standing overnight to isolate precipitate and both solids were dried in vacuo. The first crop was pure with the second crop material showing a very minor impurity (isolated broad signal 3.5 ppm not seen in first crop) but was otherwise identical. Solid first crop (28.4 g), solid second crop (3.42 g).

$^1$H NMR (CDCl$_3$): 8.01 (1H, s), 5.98 (2H, broad s), 5.70 (1H, dd), 4.16 (1H, m), 3.78 (1H, m), 2.15-1.60 (6H, overlapping m).

Preparation 2

To a solution of 2,6-dichloropurine (commercially available, for example, from Aldrich) (25 g) in dry ethyl acetate (200 mL) was added p-toluenesulfonic acid monohydrate (235 mg). The reaction was heated to 50° C. and 3,4-dihydro-2H-pyran (commercially available, for example, from Aldrich) (18.1 mL) was added in one go. The reaction was allowed to stir at 50° C. for 1 hour and the solvent was removed under reduced pressure. This afforded a yellow solid. A suspension of this solid (~36 g) in 2.0M ammonia in isopropanol (460 mL) was heated under nitrogen at 60° C. for 4 hours with an attached condenser. The reaction was poured into water (50 mL) and left to cool overnight. The precipitate was filtered and dried on a rotary evaporator (60° C.) for 30 minutes to afford the title compound as an off-white solid, 31 g (93%, 2 steps).

MS calculated for (C$_{10}$H$_{12}$ClN$_5$O)$^+$=254, 256
MS found (electrospray): (M)$^+$=254, 256 (3:1)
$^1$H NMR ((CD$_3$)$_2$SO): δ 8.43 (1H, s), 7.82 (2H, s), 5.55 (1H, dd), 4.00 (1H, m), 3.69 (1H, m), 2.21 (1H, m), 1.95 (2H, m), 1.74 (1H, m), 1.56 (2H, m).

Intermediate 3

2-Butoxy-9-(tetrahydro-2H-pyran-2-yl)-9H-purin-6-amine

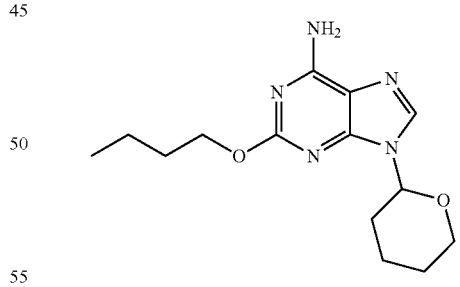

To butan-1-ol (commercially available, for example, from Aldrich) (76 mL) was added portion wise sodium tert-butoxide (15.2 g) (Note: reaction mixture gets warm). The above was stirred until homogeneous (~15 min) before 2-chloro-9-(tetrahydro-2H-pyran-2-yl)-9H-purin-6-amine (for example, as prepared for Intermediate 2) (10.0 g) was then added to the resultant pale yellow solution. The reaction mixture was then heated to 100° C., overnight. The reaction mixture was stripped to remove as much butan-1-ol as possible before being partitioned between diethyl ether and water. The diethyl ether phase was separated and the aqueous re-extracted further with diethyl ether. Combined organic layers dried over magnesium sulphate (anhydrous). Magnesium sulphate was filtered off and filtrate stripped to give brown viscous oil which was azeotroped with toluene (3 times) and placed under high vacuum overnight, transferred to new flask with dichloromethane and stripped, placed under high vacuum to give the title compound as a brown glass (9.45 g).

$^1$H NMR (CDCl$_3$): 7.85 (1H, s), 5.92 (2H, broad s), 5.64 (1H, d), 4.32 (2H, t), 4.14 (1H, m), 3.75 (1H, m), 2.10-1.95 (3H, overlapping m), 1.81-1.58 (5H, overlapping m), 1.50 (2H, m), 0.97 (3H, t).

Intermediate 4

8-Bromo-2-butoxy-9-(tetrahydro-2H-pyran-2-yl)-9H-purin-6-amine

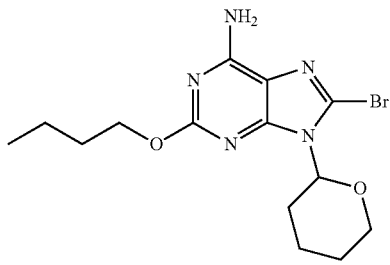 [SMILES: CCCCOc1nc(N)c2nc(Br)n(C3CCCCO3)c2n1]

2-(Butoxy)-9-(tetrahydro-2H-pyran-2-yl)-9H-purin-6-amine (for example, as prepared for Intermediate 4) (9.45 g) was dissolved in chloroform (50 mL) and cooled to 0° C. (ice-bath). To this solution was added portion wise N-bromosuccinimide (commercially available, for example, from Aldrich) (6.07 g) keeping the temperature below 3° C. This gave a dark green solution, stirred at 2.5° C. for 30 minutes before allowing to warm to room temperature and then stirring for 6 hours. The reaction mixture was then washed with water (100 mL, twice). The organic phase was dried/separated using a hydrophobic frit and evaporated to give a dark brown gum which was purified by silica chromatography (120 g) (ISCO) using a gradient elution of 0-50% ethyl acetate: cyclohexane to afford the title compound as a pale yellow solid (8.37 g).

$^1$H NMR (CDCl$_3$): 5.61 (1H, dd), 5.49 (2H, broad s), 4.32 (2H, m), 4.17 (1H, m), 3.71 (1H, m), 3.04 (1H, m), 2.11 (1H, broad d), 1.89-1.45 (6H, overlapping m), 1.50 (2H, m), 0.97 (3H, t).

Intermediate 5

2-Butoxy-8-methoxy-9-(tetrahydro-2H-pyran-2-yl)-9H-purin-6-amine

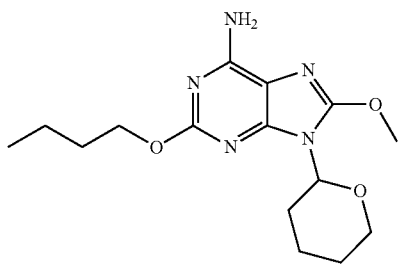 [SMILES: CCCCOc1nc(N)c2nc(OC)n(C3CCCCO3)c2n1]

8-Bromo-2-(butoxy)-9-(tetrahydro-2H-pyran-2-yl)-9H-purin-6-amine (for example, as prepared for Intermediate 4) (8.37 g) was heated to reflux with 25% sodium methoxide in methanol (commercially available, for example from Aldrich) (14.4 mL) and methanol (65 mL) for 4.5 hours. The reaction mixture was concentrated under reduced pressure and partitioned between ethyl acetate and saturated ammonium chloride solution. Separated organic phase and repeated extraction into ethyl acetate. The organic phases were combined and washed with brine (twice). The organic phase was passed through a hydrophobic frit after separating aqueous and was evaporated to give a light brown gum which was placed under high vacuum to give a foam (7.52 g) which collapsed to a gum (7.34 g) at ambient pressure and solidified overnight to give the title compound as a yellow amorphous solid.

MS calculated for $(C_{15}H_{23}N_5O_3)^+$=321

MS found (electrospray): $(M+H)^+$=322

$^1$H NMR (CDCl$_3$): 5.50 (1H, dd), 5.17 (2H, broad s), 4.29 (2H, t), 4.12 (3H, s and 1H, m), 3.70 (1H, m), 2.77 (1H, m), 2.05 (1H, m), 1.82-1.63 (6H, overlapping m), 1.50 (2H, m), 0.97 (3H, t).

Intermediate 6

2-Butoxy-8-methoxy-9H-purin-6-amine trifluoroacetate salt

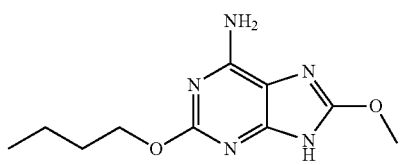 [SMILES: CCCCOc1nc(N)c2nc(OC)[nH]c2n1]

To a solution of 2-(butoxy)-8-(methoxy)-9-(tetrahydro-2H-pyran-2-yl)-9H-purin-6-amine (for example, as prepared for Intermediate 5) (7.34 g) in methanol (100 mL) was added trifluoroacetic acid (10 mL). The mixture was stirred at ambient temperature over the weekend to give a suspension. The reaction mixture was concentrated to a small volume (thick slurry) before being diluted with ethyl acetate (50 mL). The resultant slurry was filtered and washed with a small volume of ethyl acetate until the filtrate was colourless. The solid remaining was dried by air and then in vacuo to give the title compound as a white solid (6.20 g). The filtrate obtained previously was concentrated to give a slurry which was diluted with a small volume of ethyl acetate (10 mL) and then filtered and dried as above. This second crop was isolated as a white solid (0.276 g). Both crops were identical by NMR.

MS calculated for $(C_{10}H_{15}N_5O_2)^+$=237

MS found (electrospray): $(M+H)^+$=238

¹H NMR (CD₃OD): 4.47 (2H, t), 4.15 (3H, s), 1.80 (2H, m), 1.50 (2H, m), 0.99 (3H, t) (exchangeable NH₂, NH and COOH protons not observed).

Intermediate 7

N²-Butyl-9-(tetrahydro-2H-pyran-2-yl)-9H-purine-2,6-diamine

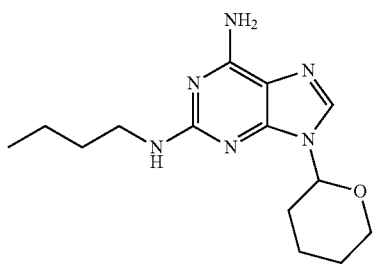 [SMILES: CCCCNc1nc(N)c2ncn(C3CCCCO3)c2n1]

To a solution of 2-chloro-9-(tetrahydro-2H-pyran-2-yl)-9H-purin-6-amine (for example, as prepared for Intermediate 2) (10 g) in dry ethylene glycol (commercially available, for example, from Aldrich) (50 mL) at room temperature and under nitrogen was added n-butylamine (commercially available, for example, from Aldrich) (16 mL) in one go. The reaction was heated at 120° C. overnight. The reaction was cooled to room temperature, diluted with ethyl acetate (150 mL) and washed with water (2×50 mL). The organic layer was dried over MgSO₄, filtered and concentrated in vacuo. This afforded the title compound as a viscous green oil (10.2 g) that was used in the next step without further purification.

MS calculated for $(C_{14}H_{22}N_6O)^+=290$

MS found (electrospray): $(M+H)^+=291$

¹H NMR ((CD₃)₂SO): δ 7.8 (1H, s), 6.6 (2H, s), 6.2 (1H, t), 5.4 (1H, dd), 4.0 (1H, m), 3.6 (1H, m), 3.2 (2H, m), 2.2 (1H, m), 1.9 (1H, m), 1.8 (1H, m), 1.7 (1H, m), (2H, m), 1.4 (2H, m), 1.3 (2H, m), 0.9 (3H, t).

Intermediate 8

N²-Butyl-8-methoxy-9H-purine-2,6-diamine, trifluoroacetic acid salt

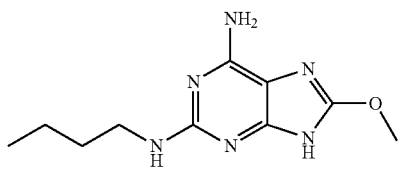 [SMILES: CCCCNc1nc(N)c2nc(OC)[nH]c2n1]

To a solution of crude N²-butyl-9-(tetrahydro-2H-pyran-2-yl)-9H-purine-2,6-diamine (for example as prepared for Intermediate 7) (~10.2 g) in dry chloroform (100 mL) at room temperature was added N-bromosuccinimide (commercially available, for example, from Aldrich) (6.3 g) in portions over 5 minutes. The dark solution was allowed to stir at room temperature for 30 minutes. The reaction mixture was washed with water (20 mL). The organic phase was passed through a hydrophobic frit and concentrated in vacuo. This afforded a beige solid which was dissolved in dry methanol (100 mL) and at room temperature under nitrogen was added sodium methoxide solution (25 wt. % in methanol, commercially available, for example, from Aldrich) (24 mL) in one go. The reaction was heated at 65° C., with a condenser attached, overnight. The reaction was cooled and concentrated in vacuo. The resultant orange residue was taken up in ethyl acetate (150 mL) and poured into saturated aqueous ammonium chloride (50 mL). The organic layer was separated and washed further with water (50 mL). The organic layer was dried over MgSO₄, filtered and concentrated in vacuo. To this material in dry methanol (70 mL) at room temperature was added trifluoroacetic acid (7 mL) in one go. The reaction was stirred for 30 hours and concentrated in vacuo to yield a dark brown solid. This was taken up in diethyl ether (20 mL) and triturated. The solid was filtered to afford the title compound as a beige solid (3.3 g, 35%, 4 steps).

MS calculated for $(C_{10}H_{16}N_6O)^+=236$

MS found (electrospray): $(M+H)^+=237$

¹H NMR ((CD₃)₂SO): δ 13.3-12.3 (1H, br.m), 8.6-7.3 (2H, m), 4.05 (3H, s), 3.28 (2H, m), 1.52 (2H, m), 1.33 (2H, m), 0.89 (3H, t) (remaining exchangeable protons not clear).

Intermediate 9

Phenylmethyl 2-(3-hydroxypropyl)-1-piperidinecarboxylate

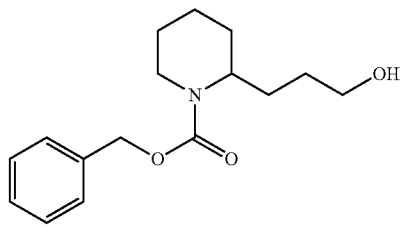 [SMILES: O=C(OCc1ccccc1)N1CCCCC1CCCO]

3-(2-Piperidinyl)-1-propanol (commercially available, for example from ChemBridge Corporation) (8.69 g, 60.7 mmol) was stirred in acetonitrile (90 mL) with triethylamine (10.40 mL, 74.6 mmol) under nitrogen and cooled in an ice bath. Benzyl chloroformate (commercially available, for example, from Aldrich) (9.53 mL, 66.7 mmol) was added dropwise. After complete addition the reaction was allowed to warm to ambient temperature and stirring then continued overnight. The suspension was filtered and the filtrate evaporated to dryness. The residue was partitioned between ethyl acetate and water. The organic phase was washed with saturated brine, passed through a hydrophobic frit and evaporated to dryness. The residue was purified by chromatography on silica (330 g silica RediSep column, loaded in DCM) using a 0-50% ethyl acetate in cyclohexane gradient over 40 minutes with a 50-100% flush of ethyl acetate on an ISCO Companion. No peaks were detected (254 nm, 280 nm) so the waste was evaporated in vacuo to recover the material. The material was re-columned using identical conditions as before but detecting at 220 nm and collecting all the eluent. The main product peak was collected and evaporated in vacuo to give the title compound as a yellow oil (6.15 g).

LCMS (System B): $t_{RET}=2.46$ min; MH⁺278

Intermediate 10

Phenylmethyl 2-(3-bromopropyl)-1-piperidinecarboxylate

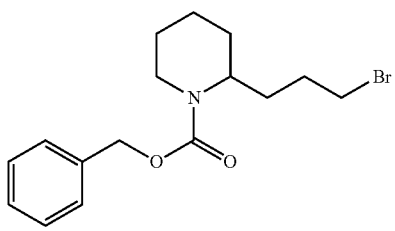 [SMILES: O=C(OCc1ccccc1)N1CCCCC1CCCBr]

To a solution of phenylmethyl 2-(3-hydroxypropyl)-1-piperidinecarboxylate (for example, as prepared for Intermediate 9) (2.14 g, 7.72 mmol) in anhydrous dichloromethane (34 mL) was added carbon tetrabromide (commercially available, for example, from Aldrich) (5.12 g, 15.43 mmol). The resulting solution was cooled in ice/water. A solution of triphenylphosphine (4.05 g, 15.43 mmol) in dry DCM (10 mL) was added dropwise over 30 minutes, producing a deep amber/brown solution. After complete addition, the reaction was allowed to warm slowly to ambient temperature and stirring continued overnight. The reaction mixture was filtered to remove the precipitate, washed with ether and the filtrate evaporated to ~10 mL. This was then loaded onto a 100 g silica cartridge and purified by chromatography using a gradient of Flashmaster 0-25% ethylacetate in cylcohexane over 40 minutes on a Flashmaster collecting all the eluent. The product peak was identified by TLC and the fractions combined and evaporated in vacuo to give the title compound as a clear oil (2.13 g)

LCMS (System B): $t_{RET}$=3.44 min; MH$^+$340/342

Intermediate 11

Phenylmethyl 2-{3-[6-amino-2-(butyloxy)-8-(methyloxy)-9H-purin-9-yl]propyl}-1-piperidinecarboxylate

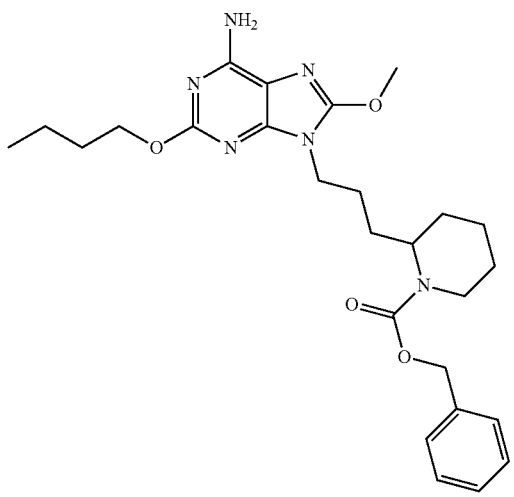 [SMILES: CCCCOc1nc(N)c2nc(OC)n(CCCC3CCCCN3C(=O)OCc3ccccc3)c2n1]

2-(Butyloxy)-8-(methyloxy)-9H-purin-6-amine, trifluoroacetic acid salt (for example, as prepared for Intermediate 6) (1.834 g, 5.22 mmol) was heated at 60° C. with potassium carbonate (2.89 g, 20.88 mmol) in DMF (23 mL) for 1 hour. Phenylmethyl 2-(3-bromopropyl)-1-piperidinecarboxylate (for example, as prepared for Intermediate 10) (2.131 g, 6.26 mmol) was added and heating continued at 50° C. overnight (20 hours). The reaction mixture was partitioned between water (250 mL) and ethyl acetate (150 mL). The aqueous was further extracted with ethyl acetate (100 mL). The combined organic layers were washed with brine (100 mL) and passed through a hydrophobic frit to dry, then stripped to dryness (rotary evaporator) to give an orange liquid. The material was loaded onto 2×70 g aminopropyl cartridge and eluted on the Flashmaster system in gradient of 0-100% ethylacetate in cyclohexane over 40 minutes. Appropriate product fractions were combined and evaporated in vacuo to give the title compound as a clear oil (1.16 g)

LCMS (System B): $t_{RET}$=2.92 min; MH$^+$497

Intermediate 12

2-(Butyloxy)-8-(methyloxy)-9-[3-(2-piperidinyl)propyl]-9H-purin-6-amine

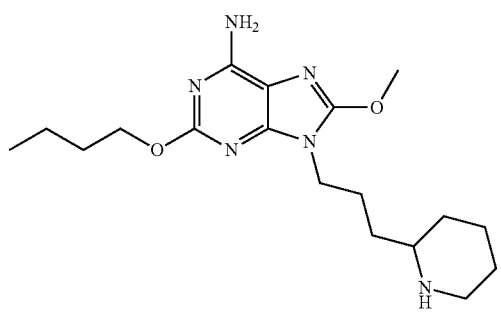 [SMILES: CCCCOc1nc(N)c2nc(OC)n(CCCC3CCCCN3)c2n1]

Phenylmethyl 2-{3-[6-amino-2-(butyloxy)-8-(methyloxy)-9H-purin-9-yl]propyl}-1-piperidinecarboxylate (for example, as prepared for Intermediate 11) (1.16 g, 2.336 mmol) in ethanol (130 mL) was hydrogenated over 10% palladium on carbon (0.497 g, 0.467 mmol) at ambient temperature overnight. The mixture was filtered through a Celite cartridge under nitrogen, washed with ethanol and evaporated in vacuo to give the title compound as a cream solid (0.66 g).

LCMS (System B): $t_{RET}$=1.29 min; MH$^+$363

Intermediate 13

Phenylmethyl 3-{[6-amino-2-(butyloxy)-8-(methyloxy)-9H-purin-9-yl]methyl}-1-piperidinecarboxylate

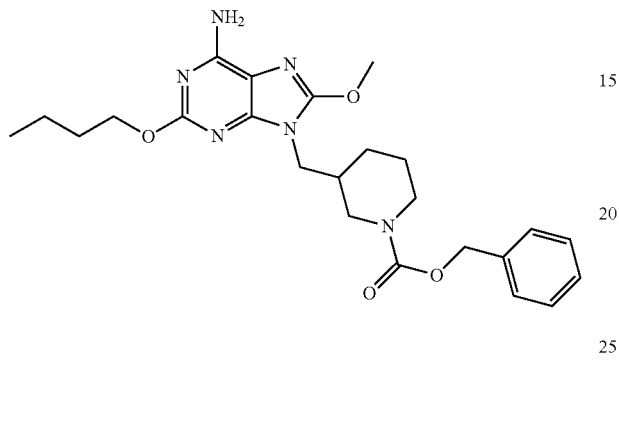

To a solution of 2-(butyloxy)-8-(methyloxy)-9H-purin-6-amine trifluoroacetate salt (for example, as prepared for Intermediate 6) (2.56 g, 7.29 mmol) in DMF (60 ml) was added potassium carbonate (4.03 g, 29.1 mmol) and the mixture was left to stir at 60° C. for one hour under an atmosphere of nitrogen. The reaction mixture was then cooled to room temperature and to this was added phenylmethyl 3-(bromomethyl)-1-piperidinecarboxylate (commercially available, for example, from AniChem, or for a prep see International Patent Application Publication Number WO1999/45006) (2.275 g, 7.29 mmol). The reaction was bought back up to 50° C. and left to stir overnight. The reaction mixture was diluted with water (~40 mL) and partitioned with a solvent mix of 1:1 ethyl acetate:DCM (40 mL). The organic layer was separated using hydrophobic frit, and was concentrated in vacuo to give pale yellow thick oil. The crude material was dissolved in 1:1 DMSO:MeOH (5 mL) and half of this solution was initially purified on reverse phase chromatography using a high pH system on a 330 g C18 silica column. The gradient used was the following:
1CV=40% Solvent B in A
2CV=60% Solvent B in A
6CV=80% Solvent B in A
1CV=95% Solvent B in A
0.2CV=95% Solvent B in A
1.8CV=100% Solvent B
Solvent A=Water with 10 mmol Ammonium Bicarbonate and $NH_3$ (pH=10), Solvent B=Acetonitrile with 0.1% $NH_3$ (CV=column volume)
The fractions which were shown to contain a required isomer by LCMS analysis were combined and concentrated in vacuo and the remaining mixed fractions were combined separately and concentrated in vacuo.
It was found that in the flask which contained the remaining half of the crude material that needed to be purified, something had precipitated. This was filtered and washed with cold DMSO to afford a white crystalline material. The mixed fractions from the chromatography were recrystallised from DMSO. Combining the material from the chromatography and the recrystallised material gave the title compound as a white solid (1.38 g).

LCMS (System C): $t_{RET}$=3.13 min; $MH^+$469

Intermediate 14

2-(Butyloxy)-8-(methyloxy)-9-(3-piperidinylmethyl)-9H-purin-6-amine

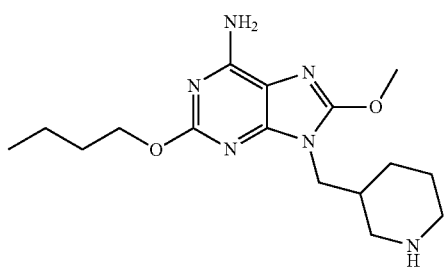 [SMILES: CCCCOc1nc(N)c2nc(OC)n(CC3CCCNC3)c2n1]

Prepared similarly to Intermediate 12 from phenylmethyl 3-{[6-amino-2-(butyloxy)-8-(methyloxy)-9H-purin-9-yl]methyl}-1-piperidinecarboxylate (for example as prepared for Intermediate 13).

LCMS (System C): $t_{RET}$=2.25 min; $MH^+$335

Intermediate 15

Phenylmethyl 3-(2-hydroxyethyl)-1-piperidinecarboxylate

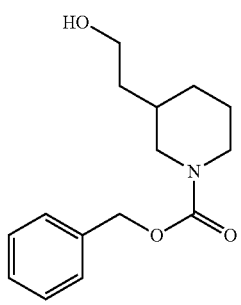 [SMILES: O=C(OCc1ccccc1)N1CCCC(CCO)C1]

Prepared similarly to Intermediate 9 from 2-(3-piperidinyl)ethanol (commercially available, for example from Tyger).

LCMS (System B): $t_{RET}$=2.32 min; $MH^+$264

Intermediate 16

Phenylmethyl 3-(2-bromoethyl)-1-piperidinecarboxylate

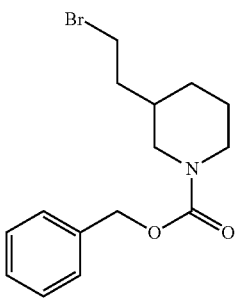 [SMILES: O=C(OCc1ccccc1)N1CCCC(CCBr)C1]

Prepared similarly to Intermediate 10 from phenylmethyl 3-(2-hydroxyethyl)-1-piperidinecarboxylate (for example, as prepared for Intermediate 15).

LCMS (System D): $t_{RET}$=3.37 min; MH$^+$326/328

Intermediate 17

Phenylmethyl 3-{2-[6-amino-2-(butyloxy)-8-(methyloxy)-9H-burin-9-yl]ethyl}-1-piperidinecarboxylate

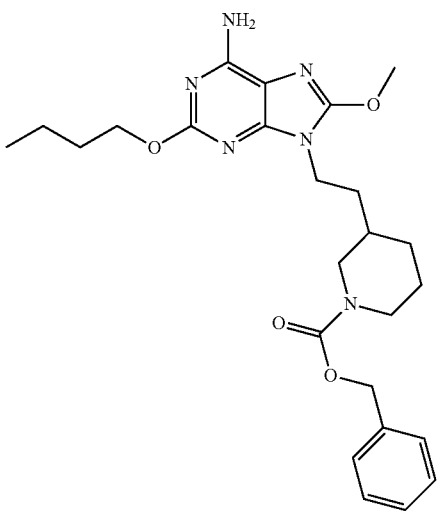 [SMILES: CCCCOc1nc(N)c2nc(OC)n(CCC3CCCN(C(=O)OCc4ccccc4)C3)c2n1]

Prepared similarly to Intermediate 11 from phenylmethyl 3-(2-bromoethyl)-1-piperidinecarboxylate (for example, as prepared for Intermediate 16) and 2-(butyloxy)-8-(methyloxy)-9H-purin-6-amine trifluoroacetate (for example, as prepared for Intermediate 6).

LCMS (System D): $t_{RET}$=3.38 min; MH$^+$483

Intermediate 18

2-(Butyloxy)-8-(methyloxy)-9-[2-(3-piperidinyl)ethyl]-9H-purin-6-amine

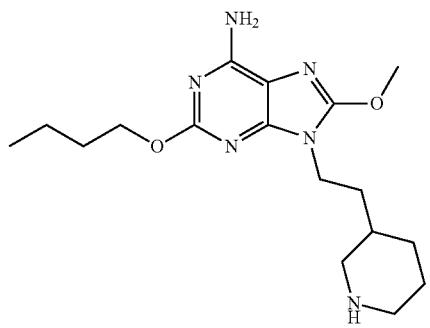 [SMILES: CCCCOc1nc(N)c2nc(OC)n(CCC3CCCNC3)c2n1]

Prepared similarly to Intermediate 12 from phenylmethyl 3-{2-[6-amino-2-(butyloxy)-8-(methyloxy)-9H-purin-9-yl]ethyl}-1-piperidinecarboxylate (for example, as prepared for Intermediate 17).

LCMS (System B): $t_{RET}$=2.42 min; MH$^+$349

Intermediate 19

Phenylmethyl 3-(3-hydroxypropyl)-1-piperidinecarboxylate

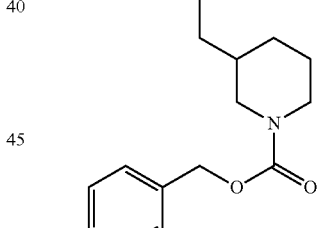

1-({[(Phenylmethyl)oxy]carbonyl}oxy)-2,5-pyrrolidinedione (commercially available, for example, from Aldrich) (8.70 g, 34.9 mmol) was added portionwise to a stirred mixture of 3-(3-piperidinyl)-1-propanol (commercially available, for example, from Astatech) (5.02 g, 35 mmol) and triethylamine (5 mL, 3.63 g, 35.9 mmol) in dichloromethane (100 mL) at room temperature. The resultant mixture was allowed to stand at room temperature for 18 hours. The reaction mixture was washed with saturated aqueous sodium hydrogen carbonate (100 mL). The organic phase was dried (MgSO$_4$), filtered and evaporated. The sample was purified by chromatography on silica (100 g cartridge loaded in dichloromethane) using a gradient of 0-100% ethyl acetate-cyclohexane over 40 minutes. The appropriate fractions were combined and evaporated in vacuo to give the title compound as a colourless liquid (8.45 g).

LCMS (System B): $t_{RET}$=2.45 min; MH$^+$278

Intermediate 20

Phenylmethyl 3-(3-bromopropyl)-1-piperidinecarboxylate

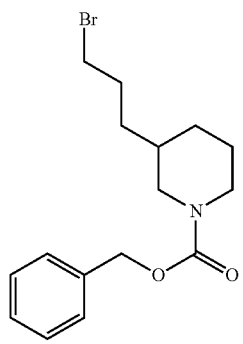 [SMILES: O=C(OCc1ccccc1)N1CCCC(CCCBr)C1]

Prepared similarly to Intermediate 10 from phenylmethyl 3-(3-hydroxypropyl)-1-piperidinecarboxylate (for example, as prepared for Intermediate 19).

LCMS (System B): $t_{RET}$=3.44 min; MH$^+$340/342

Intermediate 21

Phenylmethyl 3-{3-[6-amino-2-(butyloxy)-8-(methyloxy)-9H-burin-9-yl]propyl}-1-piperidinecarboxylate

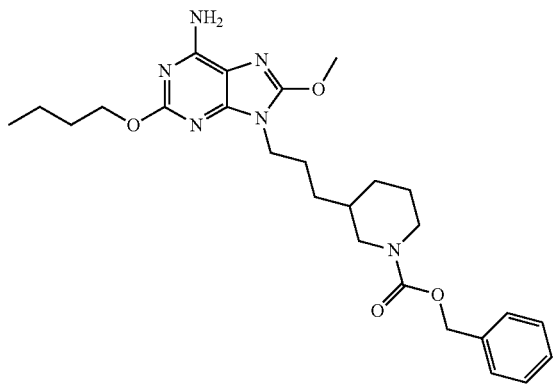 [SMILES: CCCCOc1nc(N)c2nc(OC)n(CCCC3CCCN(C(=O)OCc4ccccc4)C3)c2n1]

Prepared similarly to Intermediate 11 from 2-(butyloxy)-8-(methyloxy)-9H-purin-6-amine trifluoroacetate (for example, as prepared for Intermediate 6) and phenylmethyl 3-(3-bromopropyl)-1-piperidinecarboxylate (for example, as prepared for Intermediate 20).

LCMS (System D): $t_{RET}$=3.39 min; MH$^+$497

Intermediate 22

2-(Butyloxy)-8-(methyloxy)-9-[3-(3-piperidinyl)propyl]-9H-burin-6-amine

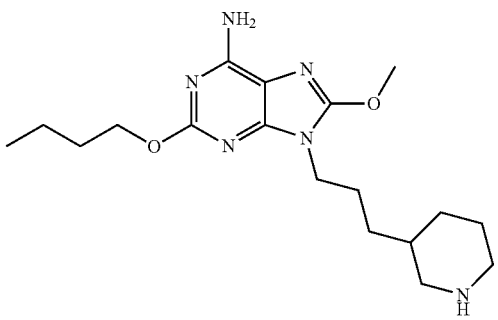 [SMILES: CCCCOc1nc(N)c2nc(OC)n(CCCC3CCCNC3)c2n1]

Prepared similarly to Intermediate 12 from phenylmethyl 3-{3-[6-amino-2-(butyloxy)-8-(methyloxy)-9H-purin-9-yl] propyl}-1-piperidinecarboxylate (for example, as prepared for Intermediate 21).

LCMS (System D): $t_{RET}$=2.43 min; MH$^+$363

Intermediate 23

Phenylmethyl 3-(4-hydroxybutyl)-1-piperidinecarboxylate

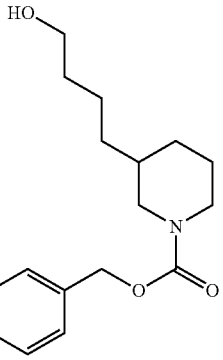

To a solution of 4-(1-{[(phenylmethyl)oxy]carbonyl}-3-piperidinyl)butanoic acid (commercially available, for example, from Astatech) (5.01 g, 16.41 mmol) in dry THF (40 mL) at 0° C. under nitrogen was added a solution of Borane-THF complex, (1M solution in THF) (49.2 mL, 49.2 mmol), dropwise over 1 hour. The mixture was allowed to stir at 0° C. and gradually allowed to warm to room temperature over 20 hours. The mixture was cooled in an ice bath and cautiously quenched with dropwise addition of MeOH (20 mL), stirred in the cold bath for 2 hours, then quenched further with 10% 2N HCl/MeOH (20 mL), stirred for 1 hour at room temperature and evaporated under reduced pressure. The residue was co-evaporated with methanol several times. The sample was purified by chromatography on silica (100 g, loaded in dichloromethane/EtOAc) using a gradient of 0-100% ethyl acetate-cyclohexane over 30 minutes collecting all 45 mL fractions on the Flashmaster II. The appropriate fractions were combined and evaporated in vacuo to give the title compound as a colourless oil (4.55 g).

LCMS (System B): $t_{RET}$=2.64 min; MH$^+$292

Intermediate 24

Phenylmethyl 3-(4-bromobutyl)-1-piperidinecarboxylate

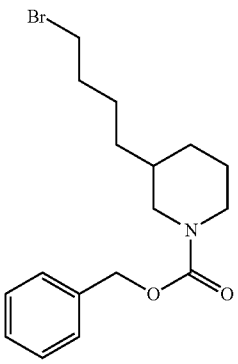 [SMILES: O=C(OCc1ccccc1)N1CCCC(CCCCBr)C1]

Prepared similarly to Intermediate 10 from phenylmethyl 3-(4-hydroxybutyl)-1-piperidinecarboxylate (for example, as prepared for Intermediate 23).

LCMS (System B): $t_{RET}$=3.62 min; MH$^+$354/356

Intermediate 25

Phenylmethyl 3-{4-[6-amino-2-(butyloxy)-8-(methyloxy)-9H-purin-9-yl]butyl}-1-piperidinecarboxylate

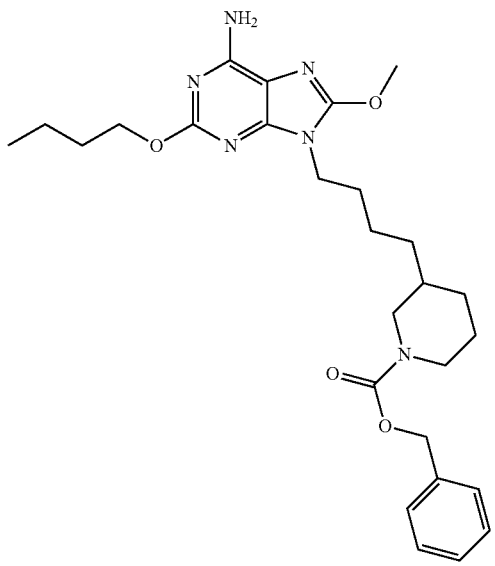 [SMILES: CCCCOc1nc(N)c2nc(OC)n(CCCCC3CCCN(C(=O)OCc4ccccc4)C3)c2n1]

Prepared similarly to Intermediate 11 from 2-(butyloxy)-8-(methyloxy)-9H-purin-6-amine trifluoroacetate (for example, as prepared for Intermediate 6) and phenylmethyl 3-(4-bromobutyl)-1-piperidinecarboxylate (for example, as prepared for Intermediate 24).

LCMS (System B): $t_{RET}$=3.08 min; MH$^+$511

Intermediate 26

2-(Butyloxy)-8-(methyloxy)-9-[4-(3-piperidinyl)butyl]-9H-burin-6-amine

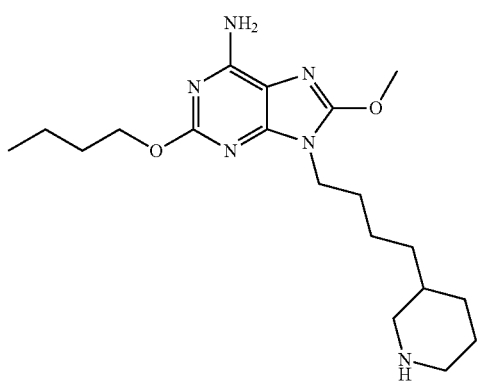 [SMILES: CCCCOc1nc(N)c2nc(OC)n(CCCCC3CCCNC3)c2n1]

Prepared similarly to Intermediate 12 from phenylmethyl 3-{-4-[6-amino-2-(butyloxy)-8-(methyloxy)-9H-purin-9-yl]butyl}-1-piperidinecarboxylate (for example, as prepared for Intermediate 25).

LCMS (System B): $t_{RET}$=1.43 min; MH$^+$377

Intermediate 27: Phenylmethyl 4-{[6-amino-2-(butyloxy)-8-(methyloxy)-9H-burin-9-yl]methyl}-1-piperidinecarboxylate

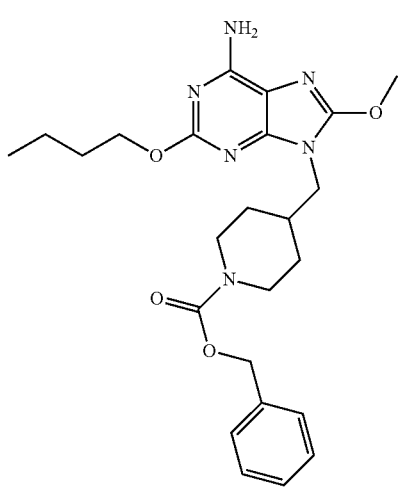 [SMILES: CCCCOc1nc(N)c2nc(OC)n(CC3CCN(C(=O)OCc4ccccc4)CC3)c2n1]

Prepared similarly to Intermediate 11 from 2-(butyloxy)-8-(methyloxy)-9H-purin-6-amine trifluoroacetate (for example, as prepared for Intermediate 6) and phenylmethyl 4-(bromomethyl)-1-piperidinecarboxylate (commercially available, for example, from Acros Organics).

LCMS (System B): $t_{RET}$=2.70 min; MH$^+$469

Intermediate 28

2-(Butyloxy)-8-(methyloxy)-9-(4-piperidinylmethyl)-9H-purin-6-amine

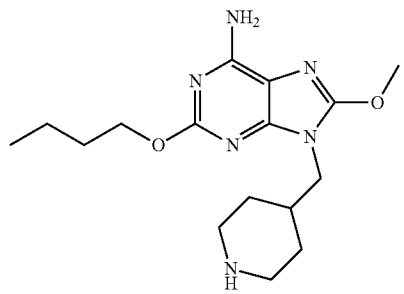 [SMILES: CCCCOc1nc(N)c2nc(OC)n(CC3CCNCC3)c2n1]

Prepared similarly to Intermediate 12 from phenylmethyl 4-{[6-amino-2-(butyloxy)-8-(methyloxy)-9H-purin-9-yl]methyl}-1-piperidinecarboxylate (for example, as prepared for Intermediate 27).

LCMS (System B): $t_{RET}$=1.13 min; MH$^+$335

Intermediate 29

Phenylmethyl 4-{2-[6-amino-2-(butyloxy)-8-(methyloxy)-9H-purin-9-yl]ethyl}-1-piperidinecarboxylate

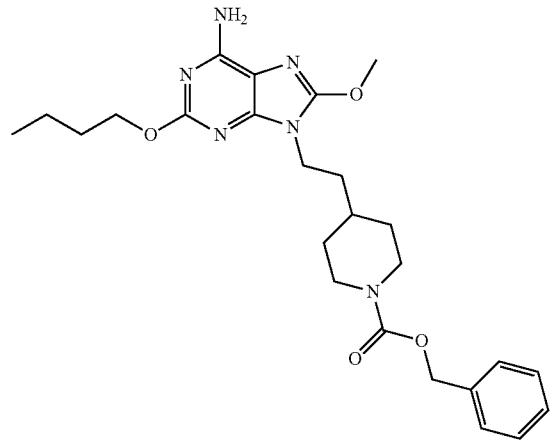 [SMILES: CCCCOc1nc(N)c2nc(OC)n(CCC3CCN(C(=O)OCc4ccccc4)CC3)c2n1]

Prepared similarly to Intermediate 11 from 2-(butyloxy)-8-(methyloxy)-9H-purin-6-amine trifluoroacetic acid salt (for example, as prepared for Intermediate 6) and phenylmethyl 4-(2-bromoethyl)-1-piperidinecarboxylate (for a preparation, see J. Med. Chem., 2003, 46(13), 2606).

LCMS (System B): $t_{RET}$=2.90 min; MH$^+$483

Intermediate 30

2-(Butyloxy)-8-(methyloxy)-9-[2-(4-piperidinyl)ethyl]-9H-purin-6-amine

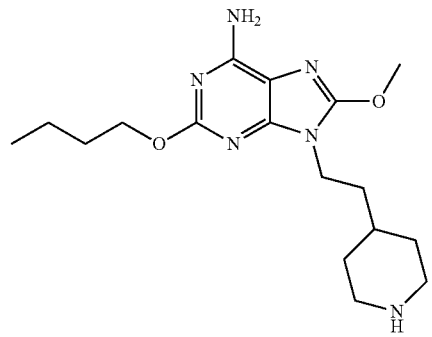 [SMILES: CCCCOc1nc(N)c2nc(OC)n(CCC3CCNCC3)c2n1]

Prepared similarly to Intermediate 12 from phenylmethyl 4-{2-[6-amino-2-(butyloxy)-8-(methyloxy)-9H-purin-9-yl]ethyl}-1-piperidinecarboxylate (for example, as prepared for Intermediate 29).

LCMS (System D): $t_{RET}$=2.23 min; MH$^+$349

Intermediate 31

Phenylmethyl 4-{3-[6-amino-2-(butyloxy)-8-(methyloxy)-9H-burin-9-yl]propyl}-1-piperidinecarboxylate

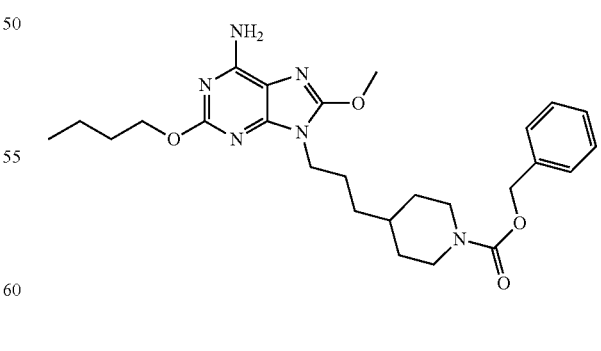

Prepared similarly to Intermediate 11 from 2-(butyloxy)-8-(methyloxy)-9H-purin-6-amine trifluoroacetic acid salt (for example, as prepared for Intermediate 6) and phenylmethyl 4-(3-bromopropyl)-1-piperidinecarboxylate (for a preparation, see J. Med. Chem., 2003, 46(13), 2606).

LCMS (System D): $t_{RET}$=3.39 min; MH$^+$497

Intermediate 32

2-(Butyloxy)-8-(methyloxy)-9-[3-(4-piperidinyl)propyl]-9H-burin-6-amine

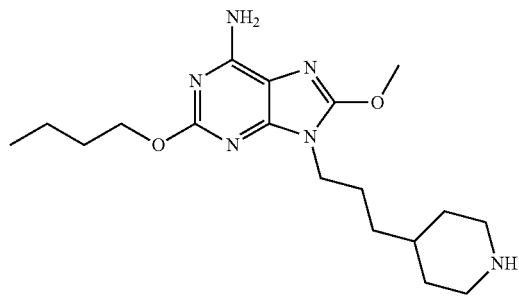 [SMILES: CCCCOc1nc(N)c2nc(OC)n(CCCC3CCNCC3)c2n1]

Prepared similarly to Intermediate 12 from phenylmethyl 4-{3-[6-amino-2-(butyloxy)-8-(methyloxy)-9H-purin-9-yl]propyl}-1-piperidinecarboxylate (for example, as prepared for Intermediate 31).

LCMS (System D): $t_{RET}$=2.39 min; MH$^+$363

Intermediate 33

Phenylmethyl 4-{4-[6-amino-2-(butyloxy)-8-(methyloxy)-9H-burin-9-yl]butyl}-1-piperidinecarboxylate

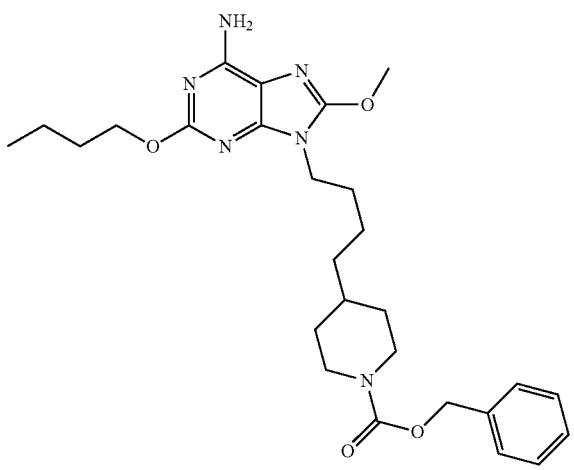 [SMILES: CCCCOc1nc(N)c2nc(OC)n(CCCCC3CCN(C(=O)OCc4ccccc4)CC3)c2n1]

Prepared similarly to Intermediate 11 from 2-(butyloxy)-8-(methyloxy)-9H-purin-6-amine trifluoroacetic acid salt (for example, as prepared for Intermediate 6) and phenylmethyl 4-(4-bromobutyl)-1-piperidinecarboxylate (for a preparation, see J. Med. Chem., 2003, 46(13), 2606).

LCMS (System B): $t_{RET}$=3.23 min; MH$^+$511

Intermediate 34

2-(Butyloxy)-8-(methyloxy)-9-[4-(4-piperidinyl)butyl]-9H-purin-6-amine

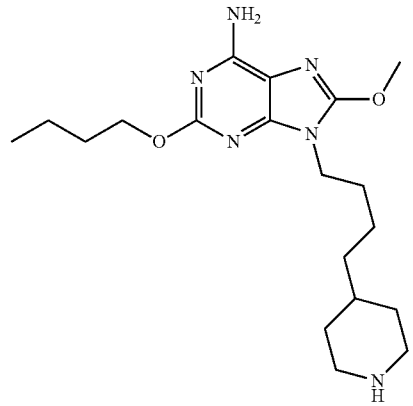 [SMILES: CCCCOc1nc(N)c2nc(OC)n(CCCCC3CCNCC3)c2n1]

Prepared similarly to Intermediate 12 from phenylmethyl 4-{-4-[6-amino-2-(butyloxy)-8-(methyloxy)-9H-purin-9-yl]butyl}-1-piperidinecarboxylate (for example, as prepared for Intermediate 33).

LCMS (System B): $t_{RET}$=1.47 min; MH$^+$377

Intermediate 35

Phenylmethyl 4-(5-bromopentyl)-1-piperidinecarboxylate

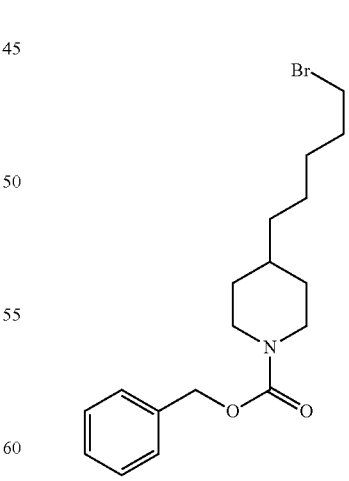

Prepared similarly to Intermediate 10 from phenylmethyl 4-(5-hydroxypentyl)-1-piperidinecarboxylate (for a preparation, see Chem. Pharm. Bull., 1986, 34(9), 3747-3761)

LCMS (System B): $t_{RET}$=3.82 min; MH$^+$368/370

Intermediate 36

Phenylmethyl 4-{5-[6-amino-2-(butyloxy)-8-(methyloxy)-9H-purin-9-yl]pentyl}-1-piperidinecarboxylate

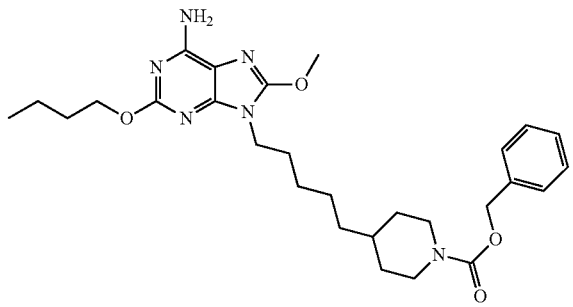 [SMILES: CCCCOc1nc(N)c2nc(OC)n(CCCCCC3CCN(C(=O)OCc4ccccc4)CC3)c2n1]

Prepared similarly to Intermediate 11 from 2-(butyloxy)-8-(methyloxy)-9H-purin-6-amine trifluoroacetic acid salt (for example, as prepared for Intermediate 6) and phenylmethyl 4-(5-bromopentyl)-1-piperidinecarboxylate (for example, as prepared for Intermediate 35).

LCMS (System B): $t_{RET}$=3.31 min; MH$^+$525

Intermediate 37: 2-(Butyloxy)-8-(methyloxy)-9-[5-(4-piperidinyl)pentyl]-9H-purin-6-amine

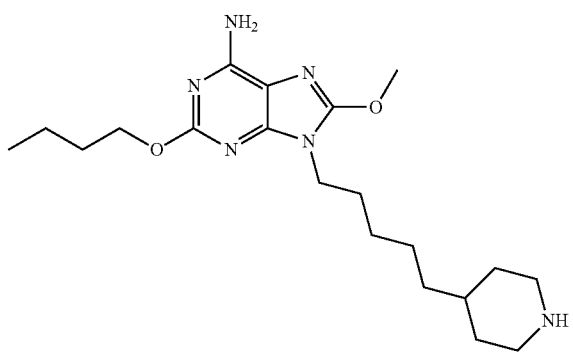 [SMILES: CCCCOc1nc(N)c2nc(OC)n(CCCCCC3CCNCC3)c2n1]

Prepared similarly to Intermediate 12 from phenylmethyl 4-{5-[6-amino-2-(butyloxy)-8-(methyloxy)-9H-purin-9-yl]pentyl}-1-piperidinecarboxylate (for example, as prepared for Intermediate 36).

LCMS (System B): $t_{RET}$=1.55 min; MH$^+$391

Intermediate 38

2-(Butyloxy)-9-(3-chloropropyl)-8-(methyloxy)-9H-purin-6-amine

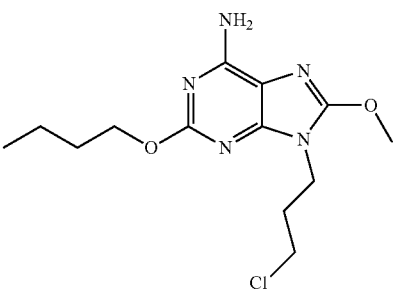 [SMILES: CCCCOc1nc(N)c2nc(OC)n(CCCCl)c2n1]

2-(Butyloxy)-8-(methyloxy)-9H-purin-6-amine trifluoroacetic acid salt (for example, as prepared for Intermediate 6) (4.7 g, 13.38 mmol) and potassium carbonate (4.62 g, 33.4 mmol) in dry DMF (50 mL) were stirred and heated at 50° C., under nitrogen, for 75 min. The mixture was allowed to cool to room temperature and then cooled to 0° C. and 1-bromo-3-chloropropane (commercially available, for example, from Aldrich) (2.106 g, 13.38 mmol) was added. The mixture was stirred at 0 to 10° C. for approximately 5 hours then allowed to warm to room temperature and stirred for approximately a further 40 hours when LCMS indicated approximately 70% of the desired product. The mixture was allowed to settle and the supernatant was pipetted off and the solvent evaporated on a rotary evaporator using a high vacuum pump at about 23° C. Chloroform and water was added to the combined residues which were stirred and the phases separated using a hydrophobic frit. The aqueous layer was re-extracted with further portions of chloroform and the combined chloroform extracts were evaporated under high vacuum at 23° C. to give a yellow solid (2.798 g). This crude material was combined with similar material obtained from two similar preparations (0.56 g and 0.995 g) and purified by flash column chromatography on silica using 2:1 ethyl acetate/chloroform as eluant to give the title compound as an off-white solid (3.011 g).

LCMS (System D): $t_{RET}$=2.79 min; MH$^+$314/316

Intermediate 39

2-(4-{3-[6-Amino-2-(butyloxy)-8-(methyloxy)-9H-purin-9-yl]propyl}-1-piperazinyl) ethanol

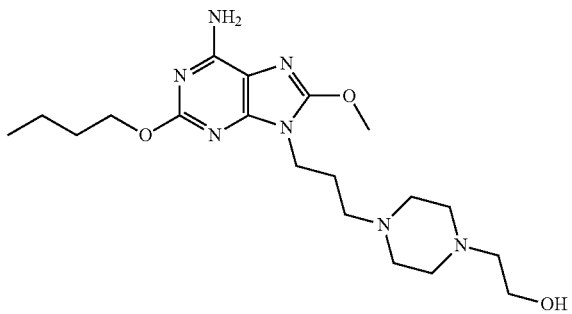 [SMILES: CCCCOc1nc(N)c2nc(OC)n(CCCN3CCN(CCO)CC3)c2n1]

2-(Butyloxy)-9-(3-chloropropyl)-8-(methyloxy)-9H-purin-6-amine (for example, as prepared for Intermediate 39) (80 mg, 0.255 mmol), DIPEA (0.134 mL, 0.765 mmol) and 2-(1-piperazinyl)ethanol (commercially available, for example, from Aldrich) (133 mg, 1.020 mmol) was heated in acetonitrile (2 mL) in a test-tube in a Radley greenhouse. The reaction was heated at 70° C. for 28 hours then allowed to cool and evaporated in vacuo. Aqueous sodium bicarbonate was added and the mixture was extracted several times with chloroform, the chloroform being filtered through a hydrophobic frit separator. The solvent was removed to give a brown gum (171 mg) which was purified on MDAP (method A). The fractions were evaporated in vacuo and the residue worked up with an aqueous sodium bicarbonate/chloroform extraction as before and the solvent removed to give the title compound as a colourless oil (80 mg).

LCMS (System D): $t_{RET}$=2.06 min; MH$^+$408

Intermediate 40

N$^2$-Butyl-9-(3-chloropropyl)-8-(methyloxy)-9H-purine-2,6-diamine

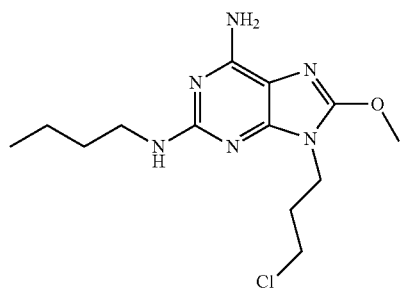 [SMILES: CCCCNc1nc(N)c2nc(OC)n(CCCCl)c2n1]

N$^2$-Butyl-8-(methyloxy)-9H-purine-2,6-diamine trifluoroacetic acid salt (for example, as prepared for Intermediate 8) (701 mg, 2.001 mmol) and potassium carbonate (690 mg, 4.99 mmol) were suspended in DMF (10 mL) and the mixture heated at 50° C. under nitrogen for 2 hours. The mixture was allowed to cool and then 1-bromo-3-chloropropane (198 µL, 2.002 mmol) was added and the reaction mixture stirred at ambient temperature overnight. After 16 hours the reaction mixture was partitioned between water and DCM (25 mL of each). The aqueous phase was extracted with further DCM (2×20 mL). The combined DCM extracts were dried over magnesium sulphate and concentrated in vacuo to give the impure title compound as a pale yellow oil with some solid present (0.76 g) which was used without further purification.

LCMS (System D): $t_{RET}$=2.75 min; MH$^+$=313/315

Intermediate 41

2-(4-{3-[6-amino-2-(butylamino)-8-(methyloxy)-9H-purin-9-yl]propyl}-1-piperazinyl) ethanol

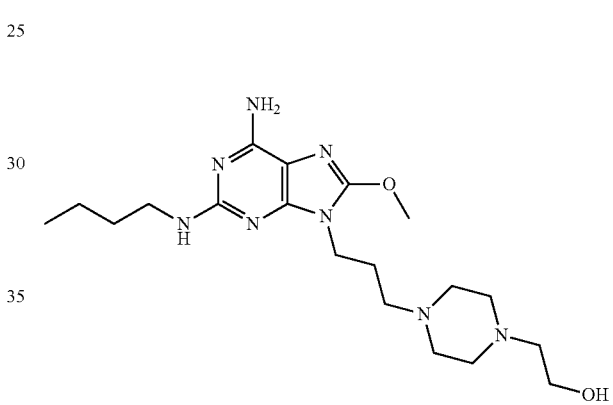

N$^2$-Butyl-9-(3-chloropropyl)-8-(methyloxy)-9H-purine-2,6-diamine (for example, as prepared for Intermediate 40) (100 mg, 0.320 mmol) (actually 120 mg used, as it contains 0.8 equivalents DMF) was weighed into a small test tube, using DMF (2 mL) to wash in. To this solution was added DIPEA (167 µL, 0.959 mmol), followed by 2-(1-piperazinyl) ethanol (commercially available, for example, from Aldrich) (78 µL, 0.636 mmol). The resulting pale yellow solution was heated at 70° C. with stirring under nitrogen for 18 hours. The reaction mixture was partitioned between water and DCM (approximately 10 mL each). The layers were separated using a hydrophobic frit and the aqueous was extracted with further DCM (2×10 mL). The combined DCM extracts were concentrated in vacuo then under nitrogen flow.

The residue (still containing DMF) was diluted to a total volume of 2 mL with MeOH and purified by MDAP (Method A). The product fractions were combined and concentrated in vacuo then under nitrogen flow to give the title compound as a colourless glass (45.9 mg).

LCMS (System D): $t_{RET}$=1.95 min; MH$^+$407

Intermediate 42

2-(Butyloxy)-9-(4-chlorobutyl)-8-(methyloxy)-9H-purin-6-amine

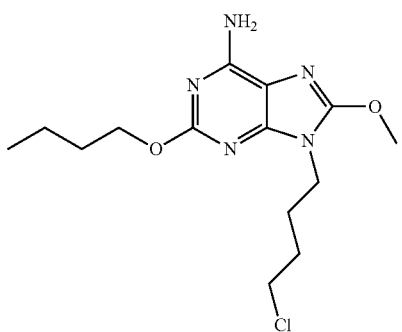 [SMILES: CCCCOc1nc(N)c2nc(OC)n(CCCCCl)c2n1]

2-(Butyloxy)-8-(methyloxy)-9H-purin-6-amine trifluoroacetate salt (for example, as prepared for Intermediate 6) (2 g, 5.69 mmol) and potassium carbonate (1.967 g, 14.23 mmol) were suspended in DMF (20 mL) and heated to 50° C., under nitrogen for 30 minutes. The mixture was cooled to room temperature, 1-bromo-4-chlorobutane (commercially available, for example, from Aldrich) (0.656 mL, 5.69 mmol) was added and stirring continued at room temperature for 20 hours. The solvent was evaporated under reduced pressure and the residue was partitioned between DCM (40 mL) and water (40 mL). The layers were separated using a hydrophobic frit and the aqueous layer washed with DCM (10 mL). The combined organic extracts were concentrated in vacuo to give crude material that was purified by silica chromatography using the Flashmaster (70 g cartridge) eluting with a cyclohexane:ethyl acetate 0-100% gradient over 30 min. The product containing fractions were combined and evaporated to give the title compound as a white solid (1.4 g).

LCMS (System D): $t_{RET}$=2.92 min; $MH^+$=328/330

Intermediate 43

$N^2$-Butyl-9-(4-chlorobutyl)-8-(methyloxy)-9H-purine-2,6-diamine

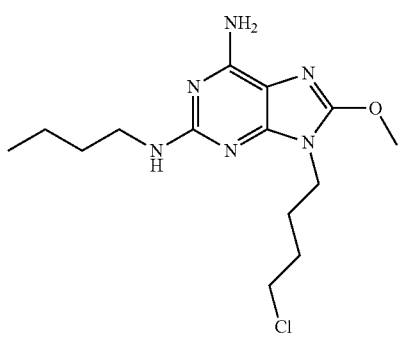 [SMILES: CCCCNc1nc(N)c2nc(OC)n(CCCCCl)c2n1]

$N^2$-Butyl-8-(methyloxy)-9H-purine-2,6-diamine trifluoroacetic acid salt (for example, as prepared for Intermediate 8) (5 g, 14.27 mmol) and potassium carbonate (4.93 g, 35.7 mmol) were suspended in DMF (40 mL) and heated to 50° C., under nitrogen for 30 minutes. The mixture was cooled to room temperature, 1-bromo-4-chlorobutane (commercially available, for example, from Aldrich) (1.645 mL, 14.27 mmol) was added and stirring was continued at room temperature for 20 hours. The solvent was concentrated under vacuum and the residue was partitioned between DCM (100 mL) and water (100 mL). The layers were separated using a hydrophobic frit and the aqueous phase was re-extracted with DCM (100 mL). The combined organics extracts were concentrated in vacuo and the residue purified by chromatography using a Flashmaster apparatus (100 g silica cartridge) and using a DCM:Methanol 0-25% gradient over 40 min. The desired fractions were combined and concentrated under vacuum to give the impure title compound as a yellow oil (5.1 g).

LCMS (System D): $t_{RET}$=2.88 min; $MH^+$=327/329

Intermediate 44

2-(Butyloxy)-9-(5-chloropentyl)-8-(methyloxy)-9H-purin-6-amine

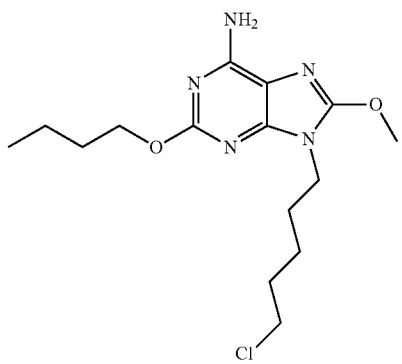 [SMILES: CCCCOc1nc(N)c2nc(OC)n(CCCCCCl)c2n1]

2-(Butyloxy)-8-(methyloxy)-9H-purin-6-amine trifluoroacetate salt (for example, as prepared for Intermediate 6) (2 g, 5.69 mmol) and potassium carbonate (1.967 g, 14.23 mmol) were suspended in DMF (20 mL) and heated to 50° C., under nitrogen for 1 hour. The mixture was cooled to room temperature, 1-bromo-5-chloropentane (commercially available, for example, from Aldrich) (0.75 mL, 5.69 mmol) was added and stirring was continued at room temperature for 18 hours. The reaction mixture was partitioned between DCM (40 mL) and water (40 mL) and the layers were separated using a hydrophobic frit. The aqueous layer was extracted again with DCM (10 mL) and the combined organics were washed with saturated lithium chloride solution, separated (hydrophobic frit)

and concentrated in vacuo to give the title compound as a yellow oil (1.946 g).

LCMS (System B): $t_{RET}$=2.58 min; MH⁺=342/344

EXAMPLES

Example 1

6-Amino-2-(butyloxy)-9-[3-[1-(2-hydroxyethyl)-2-piperidinyl]propyl]-7,9-dihydro-8H-purin-8-one

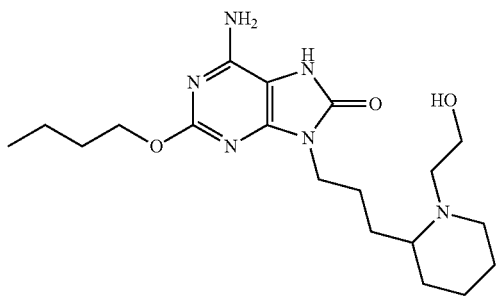 [SMILES: CCCCOc1nc(N)c2[nH]c(=O)n(CCCC3CCCCN3CCO)c2n1]

2-(Butyloxy)-8-(methyloxy)-9-[3-(2-piperidinyl)propyl]-9H-purin-6-amine (for example, as prepared for Intermediate 12) (0.036 g, 0.10 mmol) in DMF (0.5 mL) was added to 2-bromoethanol (commercially available, for example, from Aldrich) (0.0085 mL, 0.12 mmol) (dispensed as 0.12 mL of a stock solution of 1 mmol in acetonitrile (1 mL)). DIPEA (0.040 mL, 0.23 mmol) was added and the reaction mixture heated at 50° C. for 18 hours. An additional aliquot of the 2-bromoethanol solution (0.080 mL, 0.08 mmol) and DIPEA (0.040 mL, 0.23 mmol) were added and heating continued for a further 18 hours. The reaction mixture was diluted with DMSO:MeOH (0.2 mL) and the resultant solution purified by MDAP (Method A). Appropriate fractions were combined and evaporated in vacuo. The residue was dissolved in 4M HCl in dioxane (0.2 mL) and allowed to stand at room temperature for 4 hours. The solvent was dried under a stream of nitrogen in the Radleys blowdown apparatus. The residue was redissolved in methanol (0.5 mL) and applied to the top of a 0.1 g aminopropyl SPE (preconditioned with methanol, 1.5 mL). The cartridge was washed with methanol (1.5 mL). The solvent was dried under a stream of nitrogen in the Radleys blowdown apparatus to give the title compound (0.0053 g).

LCMS (System A): $t_{RET}$=0.64 min; MH⁺393

Example 2

6-Amino-2-(butyloxy)-9-{[1-(2-hydroxyethyl)-3-piperidinyl]methyl}-7,9-dihydro-8H-purin-8-one

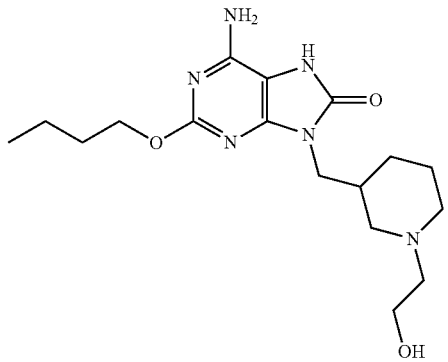 [SMILES: CCCCOc1nc(N)c2[nH]c(=O)n(CC3CCCN(CCO)C3)c2n1]

2-(Butyloxy)-8-(methyloxy)-9-piperidinylmethyl)-9H-purin-6-amine (for example, as prepared for Intermediate 14) (33.4 mg, 0.1 mmol) was suspended in DMF (0.3 mL) was added to 2-bromoethanol (commercially available, for example, from Aldrich) (0.0071 mL, 0.100 mmol). DIPEA (0.040 mL, 0.23 mmol) was added. The reaction was shaken in a stoppered vial at ambient temperature overnight. The reaction mixture was diluted with DMSO (0.4 mL) and the resultant solution purified by MDAP (Method A). Appropriate fractions were combined and evaporated in vacuo. The residues was dissolved in 4M HCl in dioxane (0.4 mL) and allowed to stand at room temperature overnight. The solvent was dried under a stream of nitrogen in the Radleys blowdown apparatus. The residue was redissolved in methanol (0.5 mL) and applied to the top of a 0.5 g aminopropyl SPE (preconditioned with methanol, 2 CV). The cartridge was washed with methanol (2 mL). The solvent was dried under a stream of nitrogen in the Radleys blowdown apparatus to give the title compound (0.022 g).

LCMS (System A): $t_{RET}$=0.57 min; MH⁺365

Example 3

6-Amino-2-(butyloxy)-9-{2-[1-(2-hydroxyethyl)-3-piperidinyl]ethyl}-7,9-dihydro-8H-purin-8-one

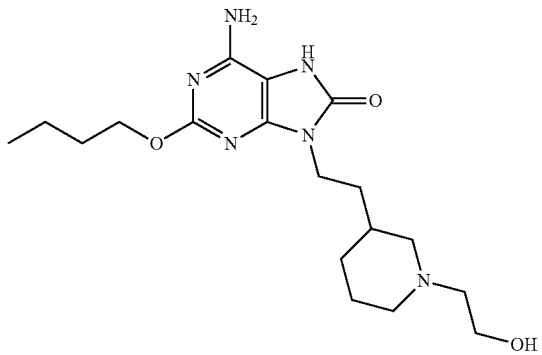 [SMILES: CCCCOc1nc(N)c2[nH]c(=O)n(CCC3CCCN(CCO)C3)c2n1]

Prepared similarly to Example 1 from 2-(butyloxy)-8-(methyloxy)-9-[2-(3-piperidinyl)ethyl]-9H-purin-6-amine (for example, as prepared for Intermediate 18) and 2-bromoethanol (commercially available, for example, from Aldrich).

LCMS (System A): $t_{RET}$=0.62 min; MH$^+$379

Example 4

6-Amino-2-(butyloxy)-9-{3-[1-(2-hydroxyethyl)-3-piperidinyl]propyl}-7,9-dihydro-8H-purin-8-one

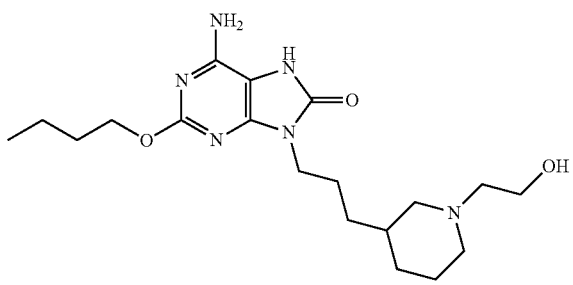 [SMILES: CCCCOc1nc(N)c2[nH]c(=O)n(CCCC3CCCN(CCO)C3)c2n1]

Prepared similarly to Example 1 from 2-(butyloxy)-8-(methyloxy)-9-[3-(3-piperidinyl)propyl]-9H-purin-6-amine (for example, as prepared for Intermediate 22) and 2-bromoethanol (commercially available, for example, from Aldrich).

LCMS (System A): $t_{RET}$=0.61 min; MH$^+$393

Example 5

6-Amino-2-(butyloxy)-9-{4-[1-(2-hydroxyethyl)-3-piperidinyl]butyl}-7,9-dihydro-8H-purin-8-one

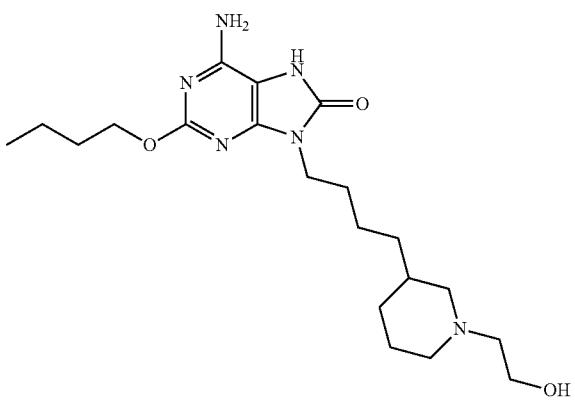 [SMILES: CCCCOc1nc(N)c2[nH]c(=O)n(CCCCC3CCCN(CCO)C3)c2n1]

Prepared similarly to Example 1 from 2-(butyloxy)-8-(methyloxy)-9-[4-(3-piperidinyl)butyl]-9H-purin-6-amine (for example, as prepared for Intermediate 26) and 2-bromoethanol (commercially available, for example, from Aldrich).

LCMS (System A): $t_{RET}$=0.66 min; MH$^+$407

Example 6

6-Amino-2-(butyloxy)-9-{[1-(2-hydroxyethyl)-4-piperidinyl]methyl}-7,9-dihydro-8H-purin-8-one

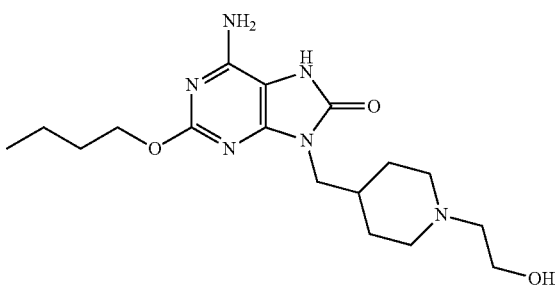 [SMILES: CCCCOc1nc(N)c2[nH]c(=O)n(CC3CCN(CCO)CC3)c2n1]

2-(Butyloxy)-8-(methyloxy)-9-(4-piperidinylmethyl)-9H-purin-6-amine (for example, as prepared for Intermediate 28) (0.0335 g, 0.10 mmol) in DMF (0.4 mL) was added to 2-bromoethanol (commercially available, for example, from Aldrich) (0.0085 mL, 0.12 mmol). DIPEA (0.040 mL, 0.23 mmol) was added and the reaction mixture heated at 50° C. for 18 hours. Additional DIPEA (0.040 mL, 0.23 mmol) was added and heating continued for a further 18 hours. The reaction mixture was diluted with DMSO:MeOH (0.25 mL) and the resultant solution purified by MDAP (Method A). Appropriate fractions were combined and evaporated in vacuo. The residue was dissolved in 4M HCl in dioxane (0.2 mL) and allowed to stand at room temperature for 4 hours. The solvent was dried under a stream of nitrogen in the Radleys blowdown apparatus. The residue was redissolved in methanol (0.5 mL) and applied to top of 0.1 g aminopropyl SPE (preconditioned with methanol, 1.5 mL). The cartridge was washed with methanol (1.5 mL). The solvent was dried under a stream of nitrogen in the Radleys blowdown apparatus to give the title compound (0.0053 g).

LCMS (System B): $t_{RET}$=1.21 min; MH$^+$365

Example 7

6-Amino-2-(butyloxy)-9-{2-[1-(2-hydroxyethyl)-4-piperidinyl]ethyl}-7,9-dihydro-8H-purin-8-one

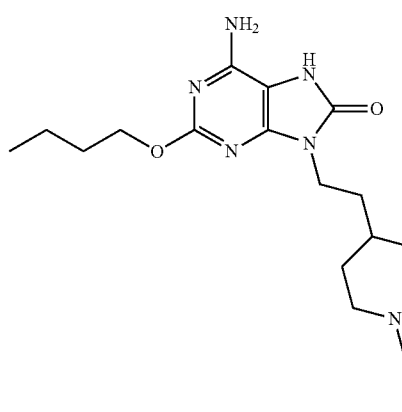

Prepared similarly to Example 1 from 2-(butyloxy)-8-(methyloxy)-9-[2-(4-piperidinyl)ethyl]-9H-purin-6-amine (for example, as prepared for Intermediate 30) and 2-bromoethanol (commercially available, for example, from Aldrich).

LCMS (System B): $t_{RET}$=1.26 min; MH$^+$379

Example 8

6-Amino-2-(butyloxy)-9-{3-[1-(2-hydroxyethyl)-4-piperidinyl]propyl}-7,9-dihydro-8H-purin-8-one

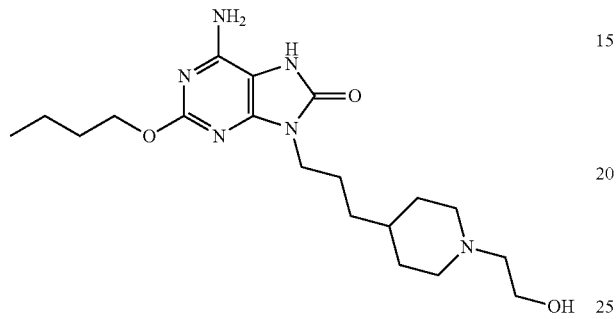

Prepared similarly to Example 1 from 2-(butyloxy)-8-(methyloxy)-9-[3-(4-piperidinyl)propyl]-9H-purin-6-amine (for example, as prepared for Intermediate 32) and 2-bromoethanol (commercially available, for example, from Aldrich).

LCMS (System A): $t_{RET}$=0.62 min; MH$^+$393

Example 9

6-Amino-2-(butyloxy)-9-{4-[1-(2-hydroxyethyl)-4-piperidinyl]butyl}-7,9-dihydro-8H-purin-8-one

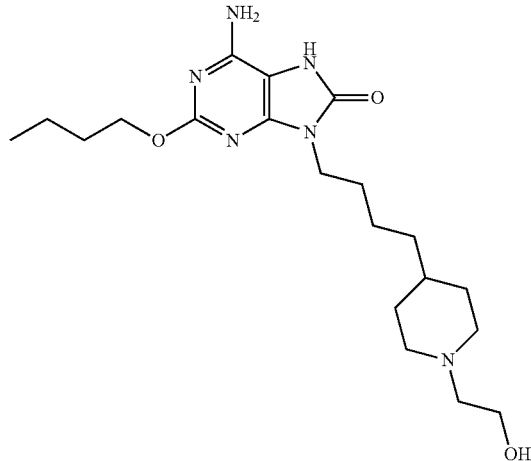 [SMILES: CCCCOc1nc(N)c2[nH]c(=O)n(CCCCC3CCN(CCO)CC3)c2n1]

2-(Butyloxy)-8-(methyloxy)-9-[4-(4-piperidinyl)butyl]-9H-purin-6-amine (for example, as prepared for Intermediate 34) (0.038 g, 0.10 mmol) in DMF (0.4 mL) was added to 2-bromoethanol (0.0085 mL, 0.12 mmol). DIPEA (0.040 mL, 0.23 mmol) was added and the reaction mixture heated at 50° C. for 18 hours. An additional aliquot of the 2-bromoethanol (commercially available, for example, from Aldrich) (0.015 mL) and DIPEA (0.040 mL, 0.23 mmol) were added and heating continued for a further 7 hours. The reaction mixture were stirred at room temperature for 72 hours then diluted with DMSO:MeOH (0.2 mL) and the resultant solution purified by MDAP (Method A). Appropriate fractions were combined and evaporated in vacuo. The residue was dissolved in 4M HCl in dioxane (0.2 mL) and allowed to stand at room temperature for 18 hours. The solvent was dried under a stream of nitrogen in the Radleys blowdown apparatus. The samples were dissolved in 1:1 MeOH:DMSO (0.6 mL) and purified by Mass Directed AutoPrep on Sunfire C18 column using Acetonitrile Water with a TFA modifier. The solvent was evaporated in vacuo. The residue was redissolved in methanol (0.5 mL) and applied to top of 0.1 g aminopropyl SPE (preconditioned with methanol, 1.5 mL). The cartridge was washed with methanol (1.5 mL). The solvent was dried under a stream of nitrogen in the Radleys blowdown apparatus to give the title compound (0.0133 g).

LCMS (System B): $t_{RET}$=1.46 min; MH$^+$407

Example 10

6-Amino-2-(butyloxy)-9-{5-[1-(2-hydroxyethyl)-4-piperidinyl]pentyl}-7,9-dihydro-8H-purin-8-one

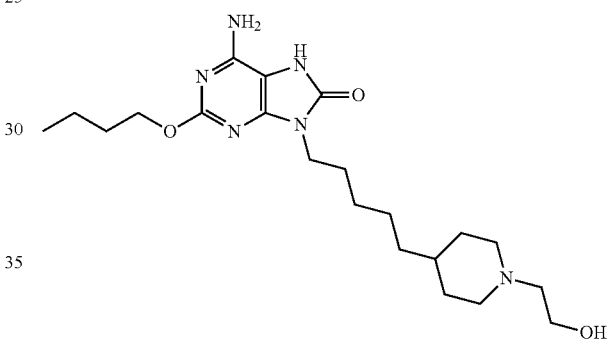

Prepared similarly to Example 1 from 2-(butyloxy)-8-(methyloxy)-9-[5-(4-piperidinyl)pentyl]-9H-purin-6-amine (for example, as prepared for Intermediate 37) and 2-bromoethanol (commercially available, for example, from Aldrich).

LCMS (System B): $t_{RET}$=1.57 min; MH$^-$ 419

Example 11

6-Amino-2-(butyloxy)-9-{3-[4-(2-hydroxyethyl)-1-piperazinyl]propyl}-7,9-dihydro-8H-purin-8-one

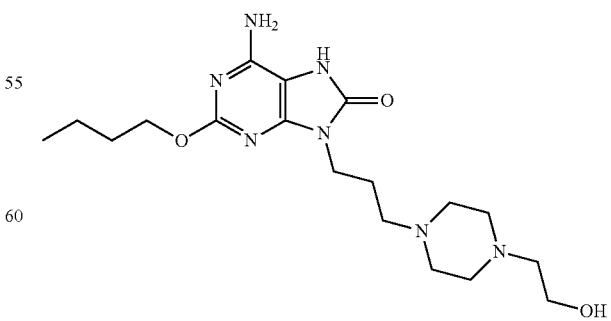

2-(4-{3-[6-Amino-2-(butyloxy)-8-(methyloxy)-9H-purin-9-yl]propyl}-1-piperazinyl)ethanol (for example, as prepared for Intermediate 39) (80 mg, 0.196 mmol) was dissolved in methanol (5.5 mL) and 4M HCl in 1,4-dioxane (1.2 mL) was added. The solution was stirred at room temperature overnight, then evaporated in vacuo. The solid residue was taken up in the minimum amount of methanol and put onto a 2 g aminopropyl SPE that had been pre-conditioned with 50 mL methanol. Appropriate fractions were evaporated in vacuo to give the title compound as a white solid (68 mg).

LCMS (System D): $t_{RET}$=1.80 min; MH$^+$394

Example 12

6-Amino-2-(butylamino)-9-[3-[4-(2-hydroxyethyl)-1-piperazinyl]propyl]-7,9-dihydro-8H-purin-8-one

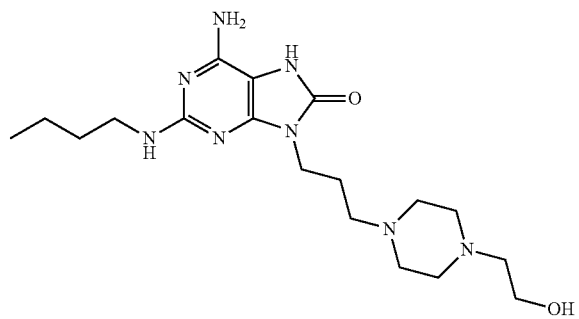 [SMILES: CCCCNc1nc(N)c2[nH]c(=O)n(CCCN3CCN(CCO)CC3)c2n1]

Prepared similarly to Example 11 from 2-(4-{3-[6-amino-2-(butylamino)-8-(methyloxy)-9H-purin-9-yl]propyl}-1-piperazinyl)ethanol (for example, as prepared for Intermediate 41).

LCMS (System D): $t_{RET}$=1.78 min; MH$^+$393

Example 13

6-Amino-2-(butyloxy)-9-{4-[4-(2-hydroxyethyl)-1-piperazinyl]butyl}-7,9-dihydro-8H-purin-8-one

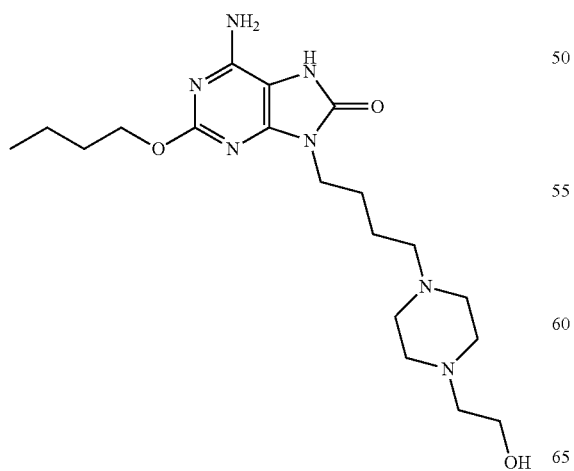

2-(Butyloxy)-9-(4-chlorobutyl)-8-(methyloxy)-9H-purin-6-amine (for example, as prepared for Intermediate 42) (100 mg, 0.305 mmol), DIPEA (0.160 mL, 0.915 mmol) and 2-(1-piperazinyl)ethanol (commercially available, for example, from Aldrich) (0.075 mL, 0.61 mmol) were dissolved in DMF (2.2 mL). The reaction mixture was stirred and heated at 50° C. under nitrogen overnight. Additional 2-(1-piperazinyl)ethanol (0.075 mL, 0.61 mmol) was added and the mixture heated at 80° C. for 20 hours. The reaction mixture was cooled down to room temp and partitioned between water (5 mL) and DCM (6 mL). The layers were separated using a hydrophobic frit and the aqueous washed with DCM (5 mL). The combined organics were concentrated under vacuum. The residues were dissolved in DMSO (1 mL) and purified by MDAP on Xbridge column using Acetonitrile Water with an ammonium carbonate modifier. The desired fractions were combined and concentrated under nitrogen blowdown. The residue was dissolved in methanol (2 mL) and HCl 4M in dioxane (3 mL) was added. The reaction mixture was stirred for 30 mins and then left in solution at room temp for 1 hour. The reaction mixture was concentrated under nitrogen blowdown and then dissolved in MeOH and eluted through an NH$_2$ (1 g). The columns were washed with MeOH (3 CV). The solvent was removed under nitrogen blowdown to give a brown solid. The samples were dissolved in DMSO (1 mL) and purified by MDAP on Xbridge column using Acetonitrile Water with an ammonium carbonate modifier. The desired fractions were combined and concentrated under nitrogen blowdown to give the title compound as a white solid (0.0262 g).

LCMS (System D): $t_{RET}$=1.89 min; MH$^+$408

Example 14

6-Amino-2-(butylamino)-9-{4-[4-(2-hydroxyethyl)-1-piperazinyl]butyl}-7,9-dihydro-8H-purin-8-one

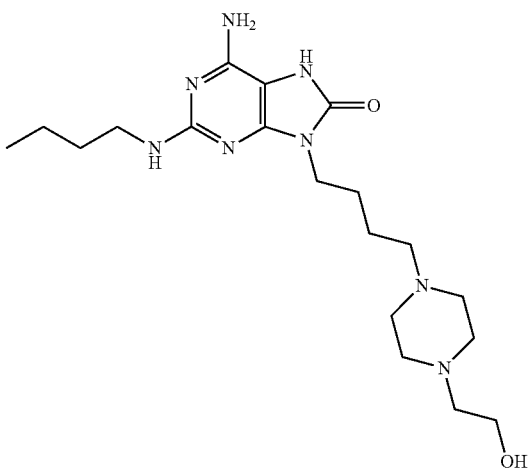 [SMILES: CCCCNc1nc(N)c2[nH]c(=O)n(CCCCN3CCN(CCO)CC3)c2n1]

Prepared similarly to Example 13 from $N^2$-butyl-9-(4-chlorobutyl)-8-(methyloxy)-9H-purine-2,6-diamine (for example, as prepared for Intermediate 43).

LCMS (System D): $t_{RET}$=1.85 min; MH$^+$407

Example 15

6-Amino-2-(butyloxy)-9-{5-[4-(2-hydroxyethyl)-1-piperazinyl]pentyl}-7,9-dihydro-8H-purin-8-one

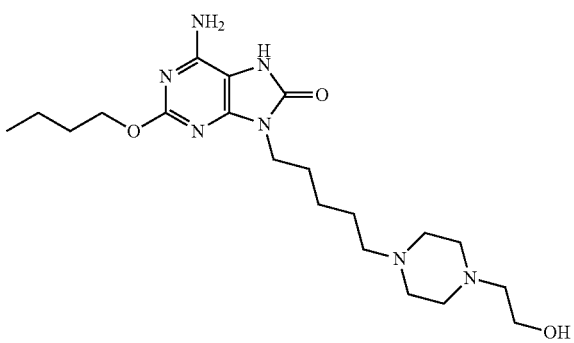 [SMILES: CCCCOc1nc(N)c2[nH]c(=O)n(CCCCCN3CCN(CCO)CC3)c2n1]

An aliquot (0.2 mL, 0.1 mmol) of a solution of 2-(butyloxy)-9-(5-chloropentyl)-8-(methyloxy)-9H-purin-6-amine (for example, as prepared for Intermediate 44) in MeCN (prepared by dissolving 410 mg, 1.2 mmol in MeCN (2.4 mL)) was added to 2-(1-piperazinyl)ethanol (commercially available, for example, from Aldrich) (0.1 mmol) in a test tube. DIPEA (50 μl, 3 equivalents) and sodium iodide (5 mg) were added. The reaction mixture was heated to 60° C. for 18 hours in a Radleys greenhouse. The samples were filtered then DMSO (0.3 mL) was added and the solution and purified MDAP on Xbridge column using Acetonitrile Water with an ammonium carbonate modifier. The solvent was evaporated in vacuo using the Genevac to give an intermediate. 2N HCl/MeOH (200 μL) added to each vial, capped and stood at room temperature for 4 hours. The solvent was dried under a stream of nitrogen in the Radleys blowdown apparatus. The residue was redissolved in methanol (0.5 mL) and applied to top of an aminopropyl SPE (0.1 g, 3 mL, preconditioned in methanol (1.5 mL)). The cartridge was washed methanol (2×1.5 mL). The solvent was removed to give the title compound (0.0175 g).

LCMS (System B): $t_{RET}$=1.11 min; MH$^+$422

Example 16

6-Amino-2-(butyloxy)-9-(5-{4-[2-(methyloxy)ethyl]-1-piperazinyl}pentyl)-7,9-dihydro-8H-purin-8-one

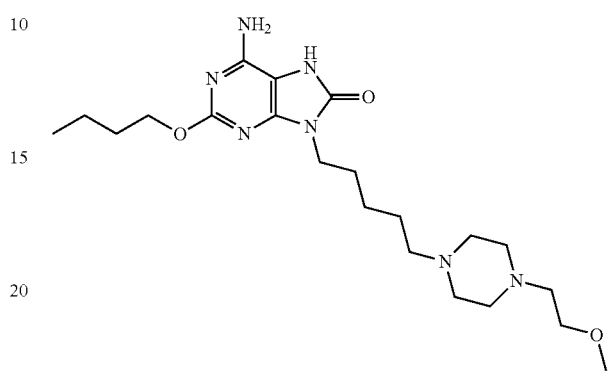

Prepared similarly to Example 15 from 2-(butyloxy)-9-(5-chloropentyl)-8-(methyloxy)-9H-purin-6-amine (for example, as prepared for Intermediate 44) and 1-[2-(methyloxy)ethyl]piperazine (commercially available, for example, from Aldrich).

LCMS (System B): $t_{RET}$=1.21 min; MH$^+$436

Example 17

6-Amino-2-(butyloxy)-9-(5-{4-[2-(ethyloxy)ethyl]-1-piperazinyl}pentyl)-7,9-dihydro-8H-purin-8-one

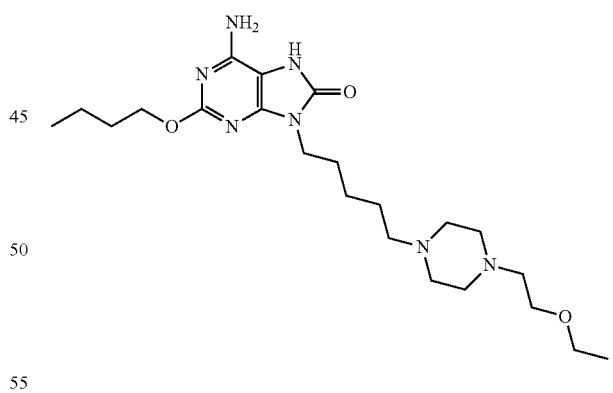

Prepared similarly to Example 15 from 2-(butyloxy)-9-(5-chloropentyl)-8-(methyloxy)-9H-purin-6-amine (for example, as prepared for Intermediate 44) and 1-[2-(ethyloxy)ethyl]piperazine (commercially available, for example, from Aldrich).

LCMS (System B): $t_{RET}$=1.28 min; MH$^+$450

Biological Data

Compounds of the invention were tested for in vitro biological activity in accordance with the following assays, or similar assays:

Assay for the Induction of Interferon-α using Cryopreserved Human Peripheral Blood Mononuclear Cells (PBMCs)
Compound Preparation Compounds were dissolved in DMSO. Serial 2-fold dilutions with DMSO were prepared and 0.25 μL dispensed into 384-well clear Greiner polypropylene plates.

Preparation of PBMCs

Blood samples of up to 200 mL were obtained from healthy human donors. Whole blood in 25 mL volumes was overlaid onto 15 mL Ficoll gradients in Leucosep tubes, and centrifuged at 1000 g for 20 minutes. Cells in the band at the plasma/histopaque interface were carefully removed and washed twice with PBS (centrifuged at 400 g for 5 min to harvest). The final pellet was resuspended in freezing medium (90% Heat-inactivated serum, 10% DMSO) to a cell concentration of $4 \times 10^7$ cells/mL. The resuspended cells were then cryopreserved (frozen) using a rate controlled freezer, and stored at −140° C. for up to 4 months.

Incubation and Assay for Interferon-α

Immediately prior to assay, vials of cryopreserved (frozen) PBMCs were thawed rapidly in a water bath at 37° C. A 1:10 dilution of the cells in trypan blue was prepared and counted. The PBMCs were then diluted in growth media [RPMI 1640 containing 10% fetal calf serum (invitrogen), Penicillin+Streptavidin (Gibco cat. #25030-024, 1:50), L-Glutamine 2 mM, and 1000 units/mL recombinant human IFN-gamma (Preprotech catalogue #300-02)] to a density of $1 \times 10^6$ cells/mL, and 50 uL/well dispensed to 384-well clear Greiner polypropylene plates containing 0.25 μL DMSO or test compound in 0.25 μL DMSO. Top final concentration of compound was typically 50 μM or 5 μM (to obtain curve fit for highly active compounds). Plates were incubated for 24 hours at 37° C. in 5% $CO_2$.

A multi-isoform immunoassay was used to quantify IFN-α in PBMC supernatants. Rabbit polyclonal antibody against human IFN-α (catalogue number 31101, Stratech Scientific) was diluted 1:10000 in assay buffer (RPMI 1640 containing 10% fetal calf serum, Invitrogen) and 20 μL was added to each well of an MSD (Meso-Scale Discovery) single small-spot 384-well GAR (goat anti-rabbit antibody coated) plate. The plate was incubated for 1 hour at room temperature with vigorous shaking. Following three washes with PBS, 20 μL of cell supernatant were added to each well of the plate. The plate was then incubated for 1 hour at room temperature with vigorous shaking. A pair of monoclonal antibodies to IFN-α (catalogue numbers 21100 and 21112, Stratech Scientific) were labelled with sulfo-TAG (MSD), diluted 1:1000 in assay buffer and 20 μL added to each well of the plate. The plate was further incubated for 1 hour at room temperature with vigorous shaking. Following three washes with PBS, 30 μL of ×2 T buffer (MSD) was added to each well and the plate was read on an MSD Sector 6000 plate reader.

Data were normalised to internal plate controls of 1 μM resiquimod (n=16) and DMSO (n=16). $pEC_{50}$ values were derived by 4-parameter curve fit with IRLS in ActivityBase, from 11-point, two-fold serial dilution of test compounds.

Results

Examples 1 to 17 had a mean $pEC_{50}$ of >5.8.

Assay for the Induction of Interferon-α and TNF-α using Fresh Human Peripheral Blood Mononuclear Cells (PBMCs)
Compound Preparation Compounds were dissolved and serially diluted in DMSO to give 100× the required concentration range using a Biomek 2000. 1 μL of test compound was transferred into 96-well tissue culture plates using a Biomek FX. Each compound was assayed in duplicate for each donor. Each plate contained a dilution series of the TLR7/8 agonist resiquimod as standard and Column 11 contained 1 μL of 200 μM resiquimod (giving a 2 μM final concentration, used to define the approximate maximal response to resiquimod).

Preparation of PBMCs

Blood samples from two human donors were collected into sodium heparin (10 U/mL). 25 mL volumes of whole blood were overlaid onto 15 mL Histopaque in Leucosep tubes which were centrifuged at 800 g for 20 min and the band at the plasma/histopaque interface carefully removed. The collected cells were centrifuged at 2500 rpm for 10 min and the pellet resuspended in 10 mL of media (RPMI 1640 (Low endotoxin) supplemented with 10% v/v foetal calf serum (FCS, low endotoxin) 100 U/mL penicillin G, 100 μg/mL streptomycin, 10 mM L-glutamine and 1× non-essential amino acids). A 1:20 dilution of the cells was prepared using trypan blue and the cells counted using a haemocytometer. The PBMCs were diluted to give a final concentration of $2 \times 10^6$/mL and 100 μL of this cells suspension was added to wells containing 1 μL of diluted test compound.

Incubation and Assays for Interferon-α and TNF-α

The cell preparations were incubated for 24 hours (37° C., 95% air, 5% $CO_2$) after which a sample of the supernatant was removed using the Biomek FX and assayed for both IFN-α and TNF-α using the MSD (Mesoscale Discovery) electrochemiluminescence assay platform. The IFN-α assay was carried out similarly to that described above. The TNF-α assay was carried out as per kit instructions (Cat No K111 BHB).

Cytokine released was expressed as a percentage of the 2 μM resiquimod control (column 11). This percentage was plotted against compound concentration and the $pEC_{50}$ for the response determined by non-linear least squares curve fitting. For the IFN-α responses generally a 4 parameter logistic model was selected. For the TNF responses where a clear maximum response was obtained (i.e. a well defined plateau in the response was observed) then a 4 parameter model was generally used. If the upper asymptote of the curve wasn't well defined then the curve fitting was generally constrained to a maximal response of 100% (i.e. to the response to 2 μM resiquimod) or to the response of the highest concentration tested if this was greater than the resiquimod response. Some curves were bell shaped for one or both cytokines and the cytokine data on the down slope of the bell shaped response (i.e. concentrations above those giving the maximal response) were generally excluded from the fit, usually with the exception of the concentration immediately above the peak response. Curve fitting thus concentrated on the up slope of the dose response curve.

Results

Example 2 showed $pEC_{50}$ for induction of IFN-α and TNF-α of 7.2 and 4.8 respectively.

Example 10 showed $pEC_{50}$ for induction of IFN-α and TNF-α of 9.3 and 5.5 respectively.

Example 17 showed $pEC_{50}$ for induction of IFN-α and TNF-α of 7.8 and 5.3 respectively.

The invention claimed is:
1. A compound of formula (I):

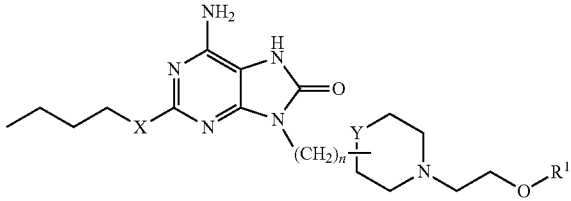

wherein;
R[1] represents hydrogen or $C_{1-3}$alkyl;
n is an integer having a value of 1 to 5;
X represents O or NH;
Y represents C or N;
or a salt thereof.

2. A compound according to claim 1 selected from the list consisting of:
6-Amino-2-(butyloxy)-9-{3-[1-(2-hydroxyethyl)-2-piperidinyl]propyl}-7,9-dihydro-8H-purin-8-one;
6-Amino-2-(butyloxy)-9-{[1-(2-hydroxyethyl)-3-piperidinyl]methyl}-7,9-dihydro-8H-purin-8-one;
6-Amino-2-(butyloxy)-9-{2-[1-(2-hydroxyethyl)-3-piperidinyl]ethyl}-7,9-dihydro-8H-purin-8-one;
6-Amino-2-(butyloxy)-9-{3-[1-(2-hydroxyethyl)-3-piperidinyl]propyl}-7,9-dihydro-8H-purin-8-one;
6-Amino-2-(butyloxy)-9-{4-[1-(2-hydroxyethyl)-3-piperidinyl]butyl}-7,9-dihydro-8H-purin-8-one;
6-Amino-2-(butyloxy)-9-{2-[1-(2-hydroxyethyl)-4-piperidinyl]ethyl}-7,9-dihydro-8H-purin-8-one;
6-Amino-2-(butyloxy)-9-{3-[1-(2-hydroxyethyl)-4-piperidinyl]propyl}-7,9-dihydro-8H-purin-8-one;
6-Amino-2-(butyloxy)-9-{4-[1-(2-hydroxyethyl)-4-piperidinyl]butyl}-7,9-dihydro-8H-purin-8-one;
6-Amino-2-(butyloxy)-9-{5-[1-(2-hydroxyethyl)-4-piperidinyl]pentyl}-7,9-dihydro-8H-purin-8-one;
6-Amino-2-(butyloxy)-9-{3-[4-(2-hydroxyethyl)-1-piperazinyl]propyl}-7,9-dihydro-8H-purin-8-one;
6-Amino-2-(butylamino)-9-{3-[4-(2-hydroxyethyl)-1-piperazinyl]propyl}-7,9-dihydro-8H-purin-8-one;
6-Amino-2-(butyloxy)-9-{4-[4-(2-hydroxyethyl)-1-piperazinyl]butyl}-7,9-dihydro-8H-purin-8-one;
6-Amino-2-(butylamino)-9-{4-[4-(2-hydroxyethyl)-1-piperazinyl]butyl}-7,9-dihydro-8H-purin-8-one;
6-Amino-2-(butyloxy)-9-{5-[4-(2-hydroxyethyl)-1-piperazinyl]pentyl}-7,9-dihydro-8H-purin-8-one;
6-Amino-2-(butyloxy)-9-(5-{4-[2-(methyloxy)ethyl]-1-piperazinyl}pentyl)-7,9-dihydro-8H-purin-8-one, and;
6-Amino-2-(butyloxy)-9-(5-{4-[2-(ethyloxy)ethyl]-1-piperazinyl}pentyl)-7,9-dihydro-8H-purin-8-one;
and salts thereof.

3. A pharmaceutically acceptable salt of a compound according to claim 1.

4. A pharmaceutically acceptable salt of a compound according to claim 2.

5. A pharmaceutical composition comprising a compound of formula (I) as defined in claim 1, or a pharmaceutically acceptable salt thereof, and optionally one or more pharmaceutically acceptable diluents or carriers.

6. A method for the treatment of asthma in a subject in need thereof which comprises administering an effective amount of a compound of formula (I) as defined in claim 1, or a pharmaceutically acceptable salt thereof.

7. A method for the treatment of asthma in a human subject in need thereof which comprises administering a vaccine composition comprising an antigen or antigen composition and a compound of formula (I) as defined in claim 1, or a pharmaceutically acceptable salt thereof.

* * * * *